(12) United States Patent
Naito et al.

(10) Patent No.: US 8,343,034 B2
(45) Date of Patent: Jan. 1, 2013

(54) ELECTRIC MEDICAL INSTRUMENT FITTING WHICH IS ATTACHED TO A MEDICAL INSTRUMENT HOLDING DEVICE

(75) Inventors: Kimihiko Naito, Hachioji (JP); Kazuo Banju, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1268 days.

(21) Appl. No.: 12/119,775

(22) Filed: May 13, 2008

(65) Prior Publication Data

US 2009/0287043 A1 Nov. 19, 2009

(51) Int. Cl.
*A61B 1/00* (2006.01)

(52) U.S. Cl. .......................... 600/102; 600/106; 600/107

(58) Field of Classification Search .................. 600/102, 600/104, 107, 114, 106, 121, 153; 700/247; 606/1, 19; 901/16
See application file for complete search history.

(56) References Cited

U.S. PATENT DOCUMENTS

| | | | | |
|---|---|---|---|---|
| 4,177,002 | A * | 12/1979 | Motoda et al. | 901/16 |
| 6,231,526 | B1 * | 5/2001 | Taylor et al. | 600/587 |
| 7,035,716 | B2 * | 4/2006 | Harris et al. | 600/102 |
| 7,273,450 | B2 * | 9/2007 | Banju | 600/102 |
| 2002/0103418 | A1 * | 8/2002 | Maeda et al. | 600/132 |
| 2005/0059960 | A1 * | 3/2005 | Simaan et al. | 606/1 |
| 2008/0065110 | A1 * | 3/2008 | Duval et al. | 606/130 |

FOREIGN PATENT DOCUMENTS

| | | |
|---|---|---|
| JP | 2004-180858 | 7/2004 |
| JP | 2005-052663 | 3/2005 |
| JP | 2006-087474 | 4/2006 |

\* cited by examiner

*Primary Examiner* — Matthew J Kasztejna
*Assistant Examiner* — Kevin G Barry, III
(74) *Attorney, Agent, or Firm* — Scully Scott Murphy & Presser, PC

(57) ABSTRACT

The electric medical instrument fitting is attached to a medical instrument holding device. The electric medical instrument fitting includes a fitting body, drive units for a plurality of second medical instruments, and an intermediate member. The fitting body has a fitting portion that enables attachment/detachment of a first medical instrument which can be arranged with an observation device and provided with channel holes for inserting treatment instruments, or which is provided with an observation device. The drive units for the second medical instruments can each be detachably connected with each second medical instrument provided with an insertion portion to be inserted into each channel hole, with a treatment portion being provided on the side of a distal end thereof. Each of the drive units for the second medical instruments is provided with a joint driver, an advancing/retreating driver and a rotation driver, for changing the position and the posture of the treatment portion. Each of the drive units for the second medical instruments has a center of gravity set at a predetermined position of a roll axis of the rotation driver, with the position of the roll axis being apart from a fitting surface by a predetermined distance. The intermediate member is arranged at the fitting body which is attached with the plurality of medical instrument drive units, a center of gravity of the entirety being set on an extension line of a center axis of the fitting portion.

10 Claims, 16 Drawing Sheets

ELECTRIC MEDICAL INSTRUMENT FITTING WHICH IS ATTACHED TO A MEDICAL INSTRUMENT HOLDING DEVICE

BACKGROUND OF THE INVENTION

1. Field of the Invention

The present invention relates to an electric medical instrument fitting which is used for a medical instrument holding device. In particular, the present invention relates to an electric medical instrument fitting for attaching an observation device and a plurality of manipulators to a holding portion of a medical instrument holding device.

2. Description of the Related Art

Recently, with the increasingly complicated endoscopic surgery, medical instrument holding devices for holding endoscopes or surgical instruments have come to be utilized. For example, Japanese Patent Application Laid-Open Publication No. 2005-52663 discloses a medical instrument holding device, which can be readily set up before operation and can be readily pulled out after operation, and which in addition can be reliably fixed to the floor surface without being rattled. In the medical instrument holding device disclosed in the literature, an endoscope can be inserted into an insertion hole of a first support arm configuring a holding portion, and held.

For treatment instruments to be inserted through treatment instrument channels of an endoscope, various manipulators comprising active joints have been contrived, for the purpose of enhancing operability for the operator. The active joints of such a manipulator include, for example, a linear motion drive joint, a roll drive joint, a yaw drive joint, a pitch drive joint, or the like. The active joints are actuated by the driving force of a drive motor provided at a driving device.

Such a manipulator is also considered to be held by a medical instrument holding device. However, in the case where an endoscope is provided with a plurality of treatment instrument channels, more medical instrument holding devices are required to hold the manipulators, which will cause the operating room to be crowded.

Thus, in a surgical system using a plurality of manipulators together with an endoscope having a plurality of treatment instrument channels, a configuration as shown in FIG. 1 can be considered.

A surgical system 200 shown in FIG. 1 includes, for example, an endoscope 201, an endoscope control unit 202, a plurality of manipulators 203 and 204, an endoscope holding device 205, and a manipulator operating device 206. The endoscope 201 has two treatment instrument channels, for example.

The endoscope 201 is held by an endoscope holder 223 provided at an arm 222 which is located farthest from a base mount 221 of the endoscope holding device 205. The manipulators 203 and 204 are inserted into the respective treatment instrument channels of the endoscope 201 held by the arm 222. As shown in the figure, a hand arm 207 and an electric cautery 208 serving as treating portions of the manipulators 203 and 204, respectively, can be projected from the ends of the channels. Under the operation of master portions 209 and 210 provided at the manipulator operating device 206, the position and posture of the hand arm 207 and the electric cautery 208 are adapted to change in response to the change of the position and posture of a master-side hand 211 and a master-side knife 212, respectively.

In the system 200, drive motors, for example, are provided at manipulator units 214 and 215. The drive motors tug and relax operation wires 213 to actuate the active joints of the manipulators 203 and 204.

SUMMARY OF THE INVENTION

The electric medical instrument fitting of the present invention is attached to a medical instrument holding device. The electric medical instrument fitting includes a fitting body, drive units for a plurality of second medical instruments, and an intermediate member. The fitting body has a fitting portion that enables attachment/detachment of a first medical instrument which can be arranged with an observation device and provided with channel holes for inserting treatment instruments, or which is provided with an observation device. The drive units for the second medical instruments can each be detachably connected with each second medical instrument provided with an insertion portion to be inserted into each channel hole, with a treatment portion being provided on the side of a distal end thereof. Each of the drive units for the second medical instruments is provided with a joint driver, an advancing/retreating driver and a rotation driver, for changing the position and the posture of the treatment portion. Each of the drive units for the second medical instruments has a center of gravity set at a predetermined position of a roll axis of the rotation driver, with the position of the roll axis being apart from a fitting surface by a predetermined distance. The intermediate member is arranged at the fitting body which is attached with the plurality of medical instrument drive units, a center of gravity of the entirety being set on an extension line of a center axis of the fitting portion.

The above and other objects, features and advantages of the invention will become more clearly understood from the following description referring to the accompanying drawings.

DETAILED DESCRIPTION OF THE PREFERRED EMBODIMENTS

With reference to the drawings, hereinafter will be described some embodiments of the present invention.

Referring to FIGS. 2 to 14, an embodiment of the present invention is described.

Figure 1:
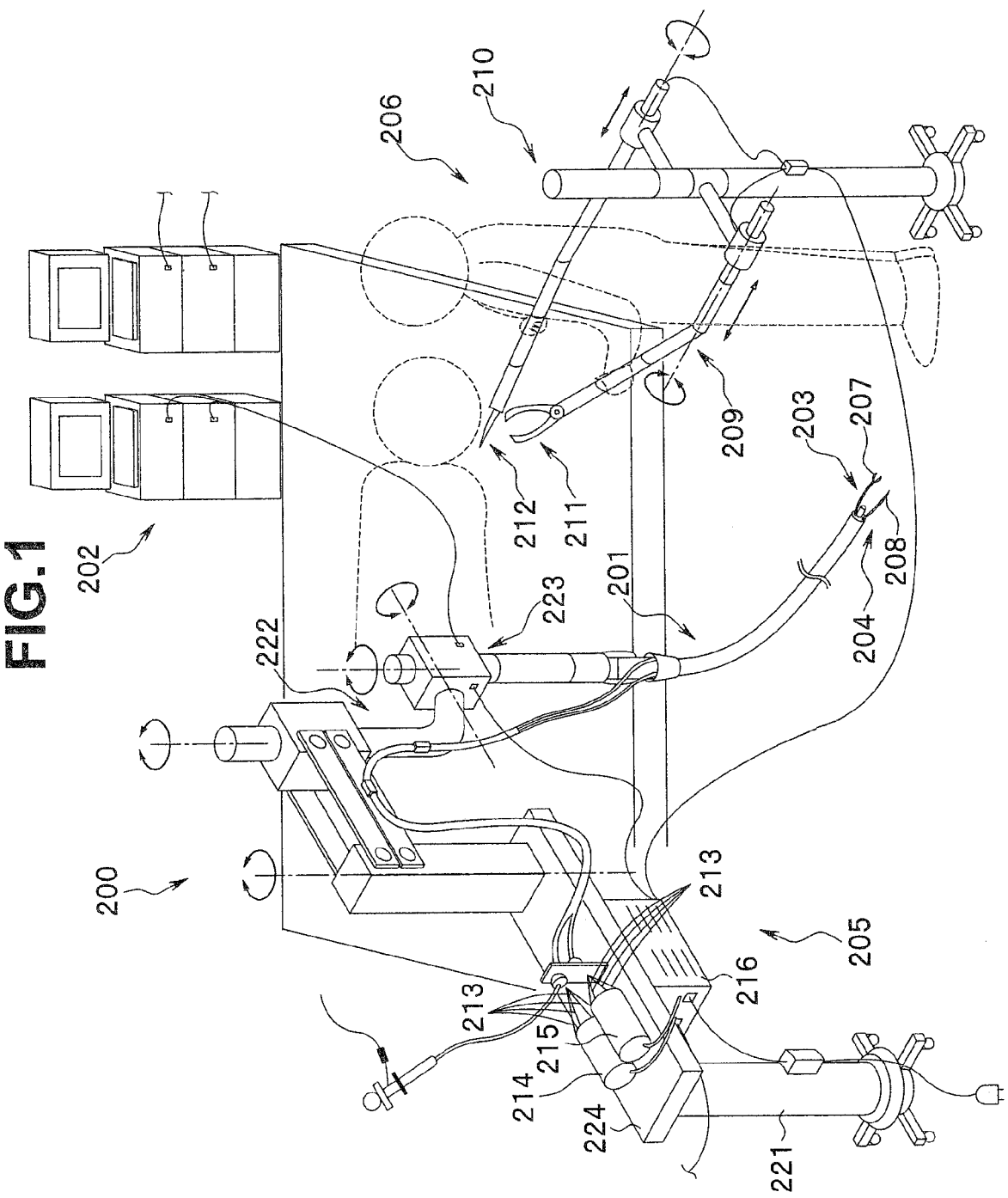
FIG. 1 is an illustration explaining an example of a configuration of a surgical system using an endoscope having treatment instrument channels and using a plurality of manipulators.
Figure 2:
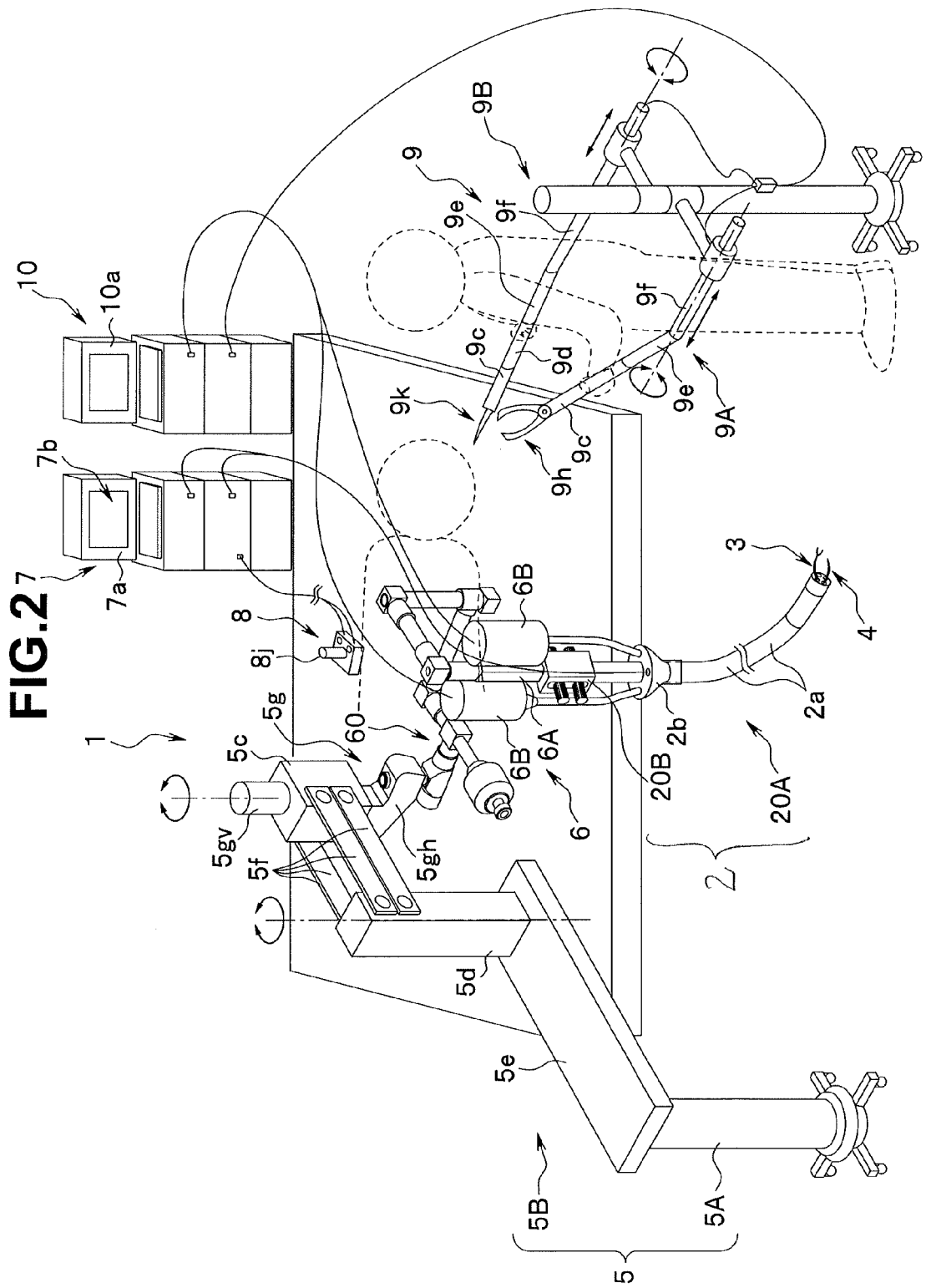
FIG. 2 is an illustration explaining a medical system having an electric medical instrument fitting of the present invention.

As shown in FIG. 2, a medical system 1 of the present embodiment includes: an observation device 2 serving as a first medical instrument; a first manipulator 3 and a second manipulator 4 serving as second medical instruments; a medical instrument holding device 5; an electric medical instrument fitting 6; an observation control unit 7; a tube bending portion operating device 8; a manipulator operating device 9; and a manipulator control unit 10.

Figure 3:
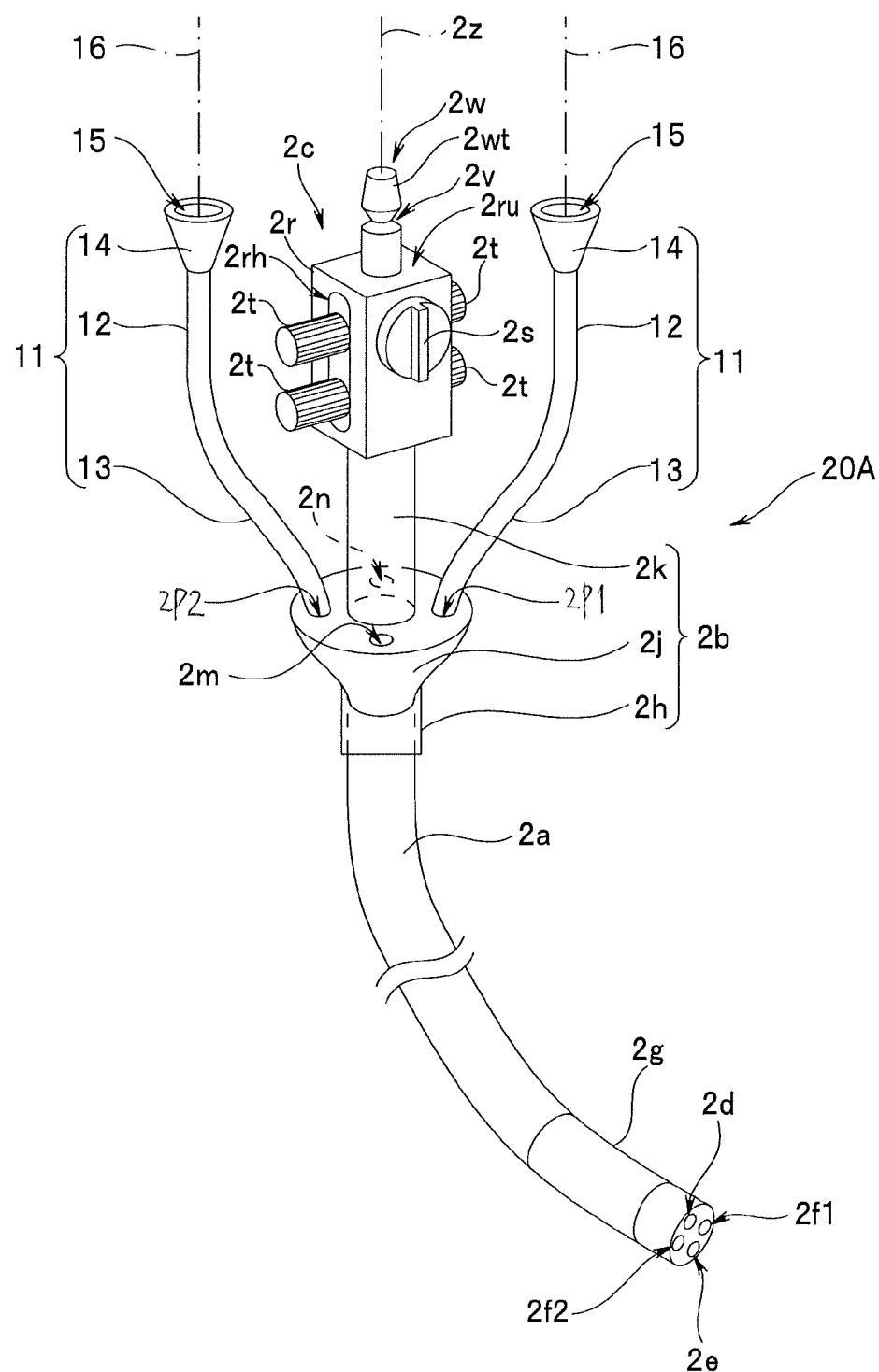
FIG. 3 is an illustration explaining a configuration of an over tube serving as a first medical instrument.

The observation device 2 includes a medical electric bending tube (hereinafter referred to as an over tube) 20A and an over tube driver 20B. As shown in FIG. 3, the over tube 20A chiefly includes a tube portion 2a, a guiding portion 2b, and an over tube driving connecting portion (hereinafter referred to as a tube connecting portion) 2c.

The tube portion 2a includes a multi-lumen tube having a plurality of through holes in the longitudinal axial direction. The multi-lumen tube is made, for example, of silicon, urethane and Teflon®.

The tube portion 2a is formed, for example, with an observation probe hole 2d, an illumination probe hole 2e, manipulator holes 2f1 and 2f2, as well as four bending operation wire insertion holes, not shown. The tube portion 2a is provided with a tube bending portion 2g having a predetermined length, at a predetermined position more proximal than a disat1 end thereof. Bending operation wires extending from the tube bending portion 2g are adapted to be inserted into the four bending operation wire insertion holes. The four bending operation wire insertion holes are arranged at an interval of 90 degrees, for example, with respect to the center axis of the tube portion 2a.

The guiding portion 2b includes a tube connecting portion 2h, a communicating portion 2j and a projected portion 2k. The tube portion 2a is connected to the tube connecting portion 2h. The communicating portion 2j has a tapered shape with its diameter increasing from the side of the tube portion toward the projected portion 2k.

Openings of guiding holes are formed in the communicating portion 2j, which guiding holes are communicated with the holes 2d, 2e, 2f1 and 2f2 provided at the tube portion 2a which is connected to the tube connecting portion 2h. The opening indicated by reference 2m is an insertion hole for the observation probe, the opening indicated by reference 2n is an insertion hole for the illumination probe, and the openings indicated by references 2P1 and 2P2 are insertion holes for the manipulators. A manipulator guiding pipe 11 is fixedly provided at each of the manipulator insertion holes 2P1 and 2P2.

The manipulator guide pipes 11 serve as second medical instrument guiding members for guiding the insertion portions (indicated by reference 48 in FIG. 6 described later) of the manipulators 3 and 4. The manipulator guide pipes 11 are hard pipes made of metal or hard resin material.

Each manipulator guide pipe 11 includes a manipulator guiding portion 12 and a manipulator introducing portion 13. In each pipe, the manipulator guiding portion 12 takes a linear shape and the manipulator introducing portion 13 having a bending section takes a curved shape. The curved shape of the manipulator introducing portion 13 contributes to the smooth introduction of the manipulator insertion portion, which will be described later, toward the manipulator holes 2f1 and 2f2 without being bent after being inserted into the manipulator guiding portion 12, that is, contributes to preventing bending of the manipulator insertion portion.

Indicated by reference 14 is a guide orifice having a large-diameter taper hole 15 on the side of its opening. Indicated by reference 16 is an extension line of the center axis of a hole for the insertion portion (hereinafter referred to as a first extension line). The first extension line 16 is an extension line of the center axis of a hole provided at the manipulator guiding portion 12. The first extension line 16 is configured to align with a roll axis of a rolling portion provided at a manipulator drive unit described later.

The tube connecting portion 2c is arranged at a proximal end surface of the projected portion 2k. Wire holes, not shown, are formed in the projected portion 2k and the communicating portion 2j. The wire holes are through holes communicating with the respective bending operation wire insertion holes formed in the tube portion 2a, and are parallel to the longitudinal axis of the guiding portion 2b.

The tube connecting portion 2c has a housing portion 2r. The housing portion 2r is provided with a pair of couplings 2s positioned face to face, and a plurality of center-of-gravity adjusting screws 2t. Further, an over tube fixing portion 2w configured by a projected portion is provided on a top surface 2ru, in the figure, of the housing portion 2r. A V-shaped groove 2v is formed in the over tube fixing portion 2w. The portion of the over tube fixing portion 2w located on the upper side of the V-shaped groove 2v is configured to have a tapered portion w2t which is thinned toward a distal end thereof. Reference 2rh indicates a long hole. Each center-of-gravity adjusting screw 2t has a screw portion introduced into the housing through the long hole 2rh, threading to a balancer 2y described later.

Pulleys and torque transmitting portions are provided in the interior of the housing portion 2r. The operation wires extending from the tube bending portion are wound about the pulleys. The torque transmitting portions include rotation transmission gears to transmit rotation of the couplings to pulleys.

A coupling 2s1 (see FIG. 5) is for causing, for example, vertical bending operation to vertically bend the tube bending portion. When the rotation of the coupling $2s1$ is transmitted to the pulley through the rotation transmission gear, the bending operation wire wound about the pulley is tugged and relaxed in response to the rotation of the coupling $2s1$, so that the tube bending portion $2g$ is bent upward or downward. On the other hand, a coupling $2s2$ (see FIG. 5) is for causing leftward rightward/leftward bending operation. That is, the bending operation wire is tugged and relaxed in response to the rotation of the coupling $2s2$ to bend the tube bending portion $2g$ leftward or rightward.

Figure 4:
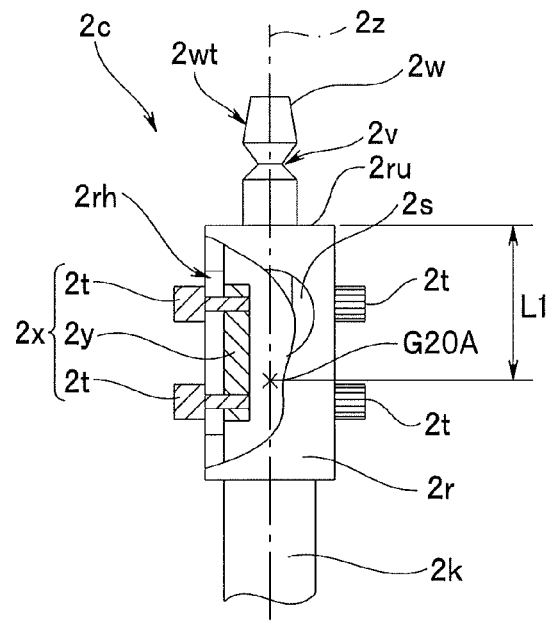
FIG. 4 is an illustration explaining a center-of-gravity adjusting mechanism provided at the over tube.

The center-of-gravity adjusting screws $2t$ configure a center-of-gravity adjusting mechanism $2x$. As shown in FIG. 4, the center-of-gravity adjusting mechanism $2x$ includes the center-of-gravity adjusting screws $2t$ and the balancer $2y$. It is so configured that release of the individual adjusting screws $2t$ can change the position of the balancer $2y$ to adjust the position of the center of gravity to a desired position.

Reference $2z$ indicates an extension line of the center axis of an over tube fitting portion (hereinafter referred to as a second extension line). The second extension line $2z$ is an extension line of the center axis of the over tube fixing portion $2w$. A center of gravity G20A of the over tube 20A is adjusted by the center-of-gravity adjusting mechanism $2x$, so as to be located at a position on the second extension line $2z$, being distanced from the top surface $2ru$ by a distance L1.

In this way, by providing the center-of-gravity adjusting mechanism in the housing portion, the position of the center of gravity of the over tube is ensured to be adjusted to a predetermined position on the second extension line, using the center-of-gravity adjusting mechanism even when, for example, the type, the number and the size of the through holes of the over tube are different, or even when the dimension of the outer diameter of the over tube is different.

Figure 5:
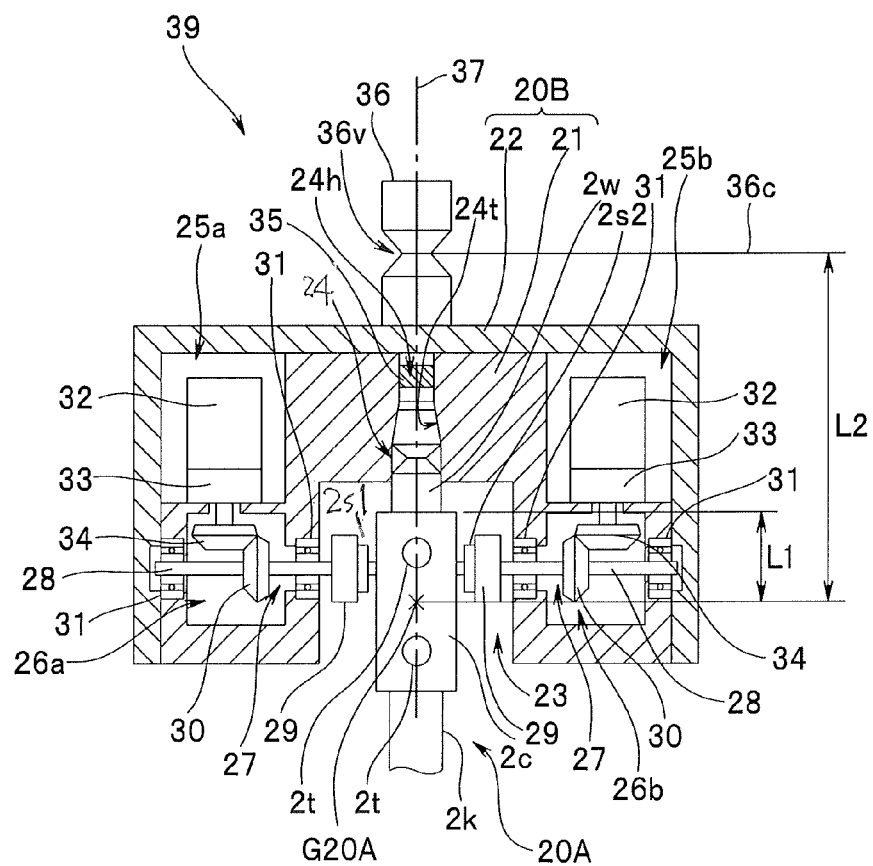
FIG. 5 is an illustration explaining a configuration of an over tube driver and a relationship with the over tube.

As shown in FIG. 5, the tube connecting portion $2c$ of the over tube 20A is connected to the over tube driver 20B. The over tube driver 20B chiefly includes a driver body 21 and an outer cover 22.

The driver body 21 is formed with a recessed portion 23 for the tube connecting portion, an over tube fitting portion 24, drive motor arranging portions 25a and 25b, and rotation transmission portion arranging portions 26a and 26b.

The rotation transmission portion arranging portions 26a and 26b are each provided with a rotation transmission mechanism 27. The rotation transmission mechanism 27 includes a shaft 28, a coupling support 29 and a transmission-side cap gear 30. The rotation transmission mechanism 27 is rotatably arranged in each of the rotation transmission portion arranging portions 26a and 26b through bearings 31.

Indicated by reference 32 are tube bending portion drive motors (hereinafter referred to as tube motors), for generating driving force for tugging the bending operation wires connected to the tube bending portion $2b$. Each tube motor 32 is provided with a motor-side cap gear 34 at a gear head shaft 33. The motor-side cap gear 34 is engaged with the transmission-side cap gear 30. The tube motors 32 are arranged in the drive motor arranging portion 25a and 25b, respectively. Specifically, the tube motor 32 arranged in the drive motor arranging portion 25a is for vertical use, and the tube motor 32 arranged in the drive motor arranging portion 25b is for lateral use.

The recessed portion 23 for the tube connecting portion is a hole where the tube connecting portion $2c$ is arranged. The over tube fitting portion 24 is a hole formed in a bottom surface of the recessed portion 23 for the tube connecting portion. The center axis of the recessed portion 23 for the tube connecting portion is formed to align with the center axis of the over tube fitting portion 24.

The over tube fixing portion $2w$ is arranged in the over tube fitting portion 24. A taper bore $24t$ is formed in the over tube fitting portion 24 to bring a tapered portion $2wt$ of the over tube fixing portion $2w$ into contact therewith. Indicated by reference $24h$ is a through hole for allowing the bottom surface of the taper bore $24t$ to communicate with the outside. A female screw is formed in the through hole $24h$, while a balance adjusting screw 35 is arranged to thread onto the female screw. The balance adjusting screw 35 is adjusted after the rotation transmission mechanisms 27 and the tube motors 32 are arranged in the driver body 21. After the center of gravity has been adjusted to position on the extension line of the center axis of the over tube fitting portion 24, the balance adjusting screw 35 is integrally fixed to the driver body 21 by adhesion, for example.

A driver fixing portion 36 configured by a projected portion is integrally provided at the outer cover 22. The driver fixing portion 36 has a V-shaped groove $36v$. The outer cover 22 is fixedly set up at the driver body 21 whose center of gravity has been adjusted. The outer cover 22 has been fabricated with the center of gravity being set, in advance, to a predetermined position.

Thus, when the outer cover 22 whose center of gravity has been preset is attached the driver body 21 whose center of gravity has been adjusted, the axis of the recessed portion 23 for the tube connecting portion and the axis of the over tube fitting portion 24 are aligned with an extension line 37 of the axis of the driver fixing portion 36 (hereinafter referred to as a third extension line). Then, the center of gravity G20A of the over tube 20A falls on the position located on the third extension line 37 and distanced by a distance L2 from a groove center $36c$ of the V-shaped groove $36v$.

In arranging the tube connecting portion $2c$ of the over tube 20A in the recessed portion 23 for the tube connecting portion of the over tube driver 20B, the over tube fixing portion $2w$ is arranged at the over tube fitting portion 24, while at the same time the couplings $2s1$ and $2s2$ are inserted into the respective opposed coupling supports 29 in an engaging manner.

The tube connecting portion $2c$ are arranged at the over tube fitting portion 24 in the state where the couplings $2s1$ and $2s2$ are inserted into the respective opposed coupling supports 29 in an engaging manner. Upon pressing a fixing screw, not shown, after bringing its distal end into contact with the V-shaped groove $2v$ of the over tube fixing portion $2w$, the tapered portion $2wt$ of the over tube fixing portion $2w$ is brought into contact with the taper bore $24t$ of the over tube fitting portion 24 to achieve integral fixation between the over tube 20A and the over tube driver 20B. In this way, a so-called electric bending over tube 39 is configured.

Figure 6:
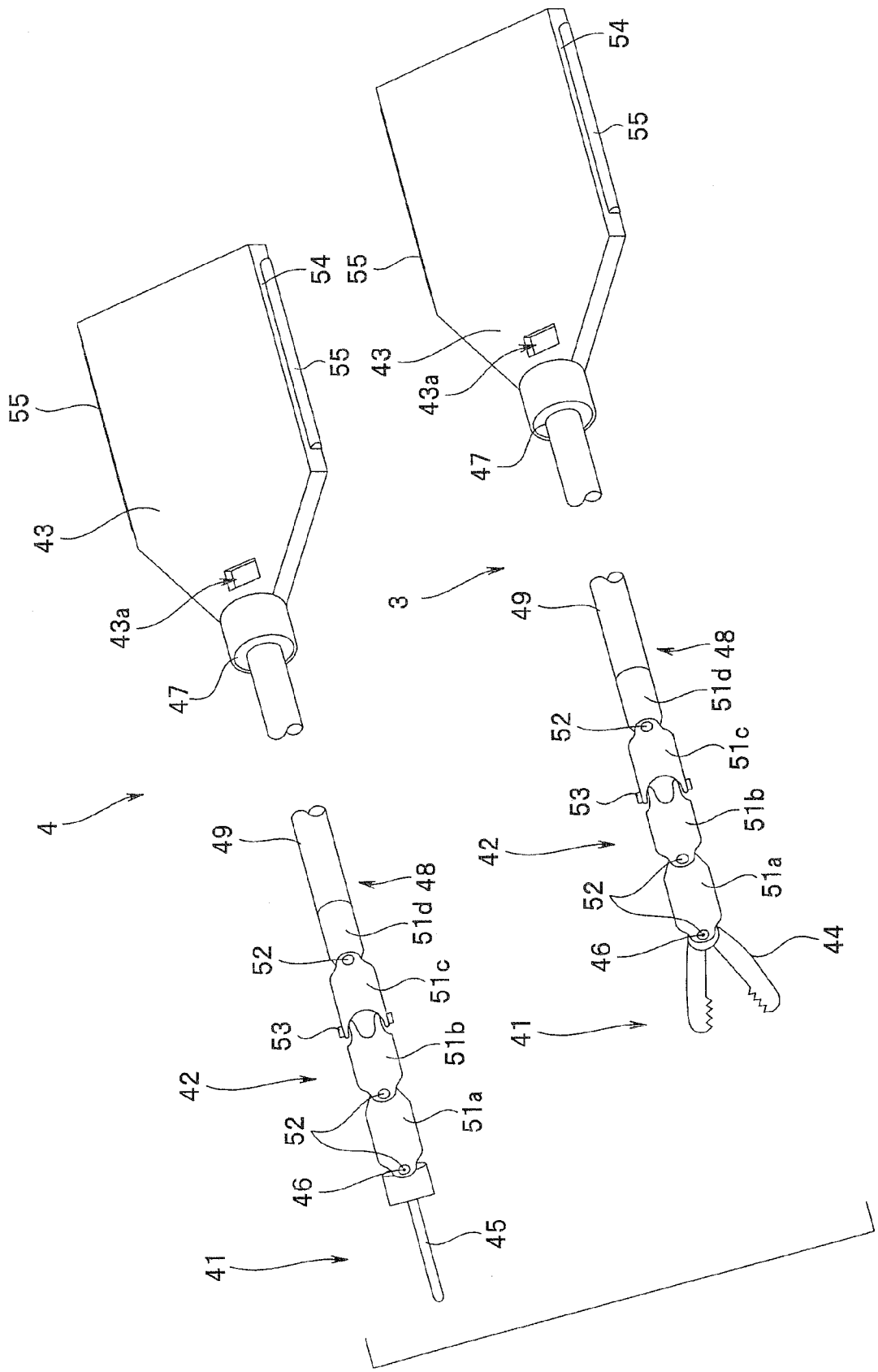
FIG. 6 is an illustration explaining configurations of a manipulator having a hand arm as a treatment portion, and a manipulator having a knife arm as a treatment portion.

Each of the manipulators 3 and 4 shown in FIG. 6 sequentially includes, from the distal side, a treatment portion 41, a manipulator bending portion 42 and a manipulator drive connecting portion (hereinafter referred to as a manipulator connecting portion) 43. The first manipulator 3 is a grasping manipulator having a hand arm 44, for example, as the treatment portion 41, while the second manipulator 4 is a high-frequency manipulator having a knife arm 45, for example, as the treatment portion 41. For example, each of the manipulators 3 and 4 includes, as active joints, a linear motion drive joint, a roll drive joint, a yaw drive joint, a pitch drive joint, or the like.

In the present embodiment, a manipulator insertion portion 48 is defined from an axial center 46 of an axis linking the treatment portion 41 of each of the manipulators 3 and 4 with the manipulator bending portion 42, to an end face 47 on the distal side of the manipulator connecting portion 43, with the length of the manipulator insertion portion 48 being set to a predetermined value.

The manipulator insertion portions 48 of the manipulators 3 and 4 are inserted into the manipulator holes 2f1 and 2f2, respectively, through the respective manipulator guide pipes 11 provided at the over tube 20A.

Each manipulator bending portion 42 includes a plurality of joint pieces 51a, 51b, 51c and 51d, which are located on the side more distal than the flexible pipe 49. The four joint pieces 51a, 51b, 51c and 51d are rotatably linked with each other through pitch drive joints 52 and a yaw drive joint 53.

A narrow side portion 54 of each manipulator connecting portion 43 is provided with a guiding portion 55 configured by a projected portion. Reference 43a indicates a click hole for the arrangement of an engaging portion which is provided at a lever configuring a manipulator drive unit described later.

Figure 7:
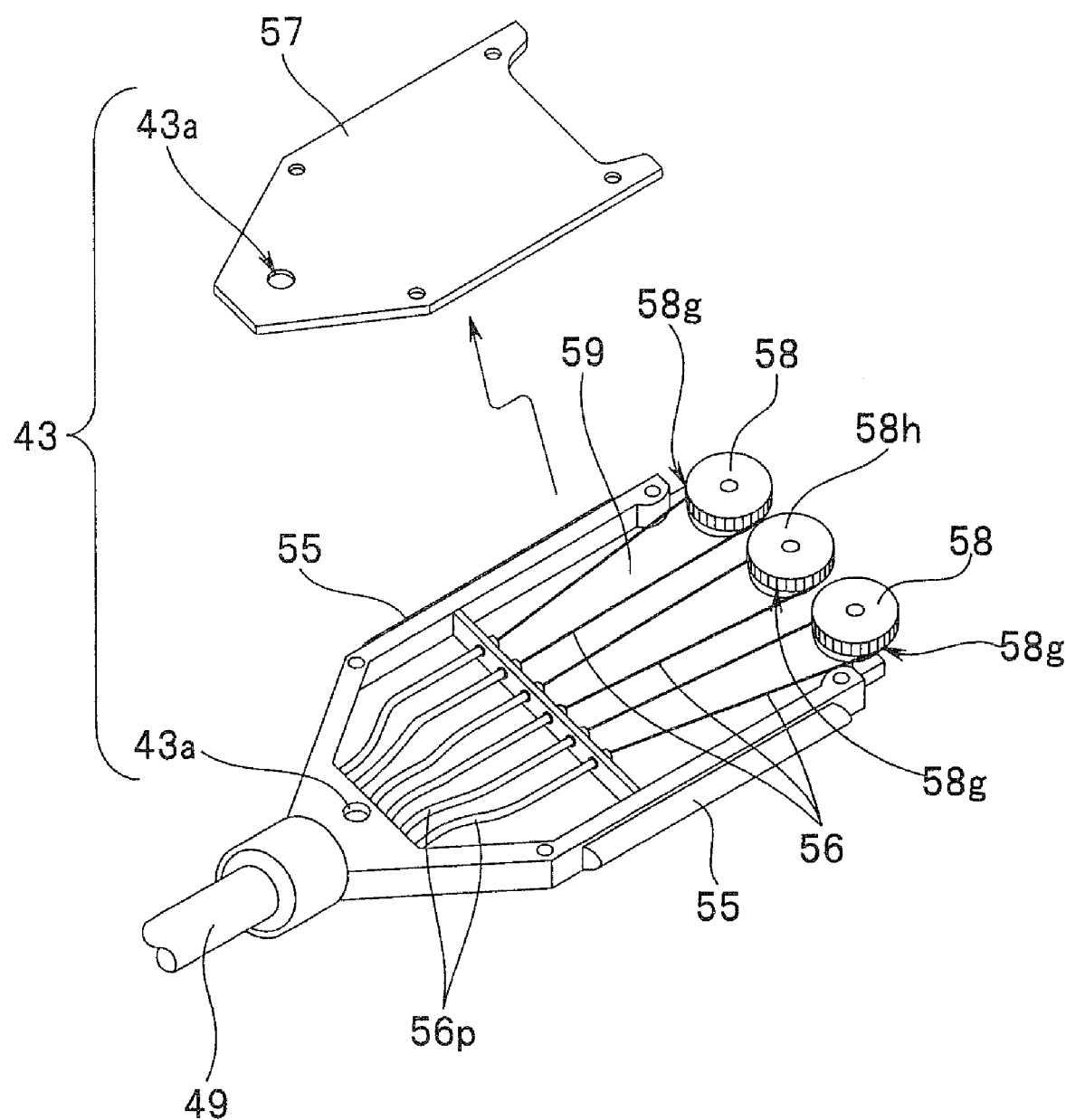
FIG. 7 is an illustration explaining a configuration of a manipulator connecting portion of a manipulator.

As shown in FIG. 7, a plurality of angle wires 56 are arranged in the interior of the manipulator connecting portion 43. The distal ends of the angle wires 56 are connected to the joints 52 and 53 and led out to the manipulator connecting portion 43 through respective coil pipes 56p. The intermediate portions of the angle wires 56 are wound about respective pulleys 58.

When the angle wires 56 are tugged/relaxed upon rotation of the pulleys 58, the positions and postures of the treatment portions 41 of the manipulators 3 and 4 are changed. The pulleys 58 are rotatably and axially supported by an intermediate plate 59 which divides the interior of the manipulator connecting portion 43 into two. The intermediate plate 59 is provided, on its rear side, with two pulleys 58 and angle wires 56, for example.

Spur gears 58g are formed in the outer peripheral surfaces of the respective pulleys 58. Specifically, the pulleys 58 are the pulleys having spur gears. Indicated by reference 57 are covers which are each provided on the side of one surface and on the side of the other surface. In the configuration of each manipulator connecting portion 43 with the attachment of the covers 57, the spur gears 58g of the pulleys 58 are exposed to the proximal side of the manipulator connecting portion 43.

It should be noted that the manipulator connecting portion 43 shown in FIG. 7 is for a grasping manipulator having the hand arm 44. For this reason, the manipulator connecting portion 43 is provided with a pulley 58h for rotating the hand arm 44. On the other hand, the second manipulator 4, which is a high-frequency manipulator, does not require such a pulley 58h for rotating the grasping portion.

Accordingly, two pulleys 58 are arranged on the side of one surface of the manipulator connecting portion 43 of the second manipulator 4. Also, the manipulator connecting portion 43 of the second manipulator 4 is provided therein with an adjusting member, not shown, for adjusting the weight and the center of gravity, instead of the pulley 58h and the angle wire 56 for the hand arm 44. A center of gravity Gm of each of the manipulators 3 and 4 is adjusted so as to be positioned on the longitudinal axis of the manipulator insertion portion 48.

The medical instrument holding device 5 shown in FIG. 2 includes a supporting portion 5A and a holding portion 5B. The holding portion 5B includes, for example, a first support arm 5c, a second support arm 5d and a third support arm 5e. The third support arm 5e is integrated into the supporting portion 5A. The second support arm 5d is vertically set up on the side of the top surface of the third support arm 5e. The second support arm 5d is arranged so as to be rotatable with respect to the third support arm 5e. The first support arm 5c is fixedly set up at the second support arm 5d through a plurality of fixing plates 5f, for example. A vertical arm portion 5gv of an L-shaped arm 5g formed into an L shape is rotatably attached to the first support arm 5c. A medical instrument holder 60 is attached to a horizontal arm portion 5gh of the L-shaped arm 5g.

Figure 8:
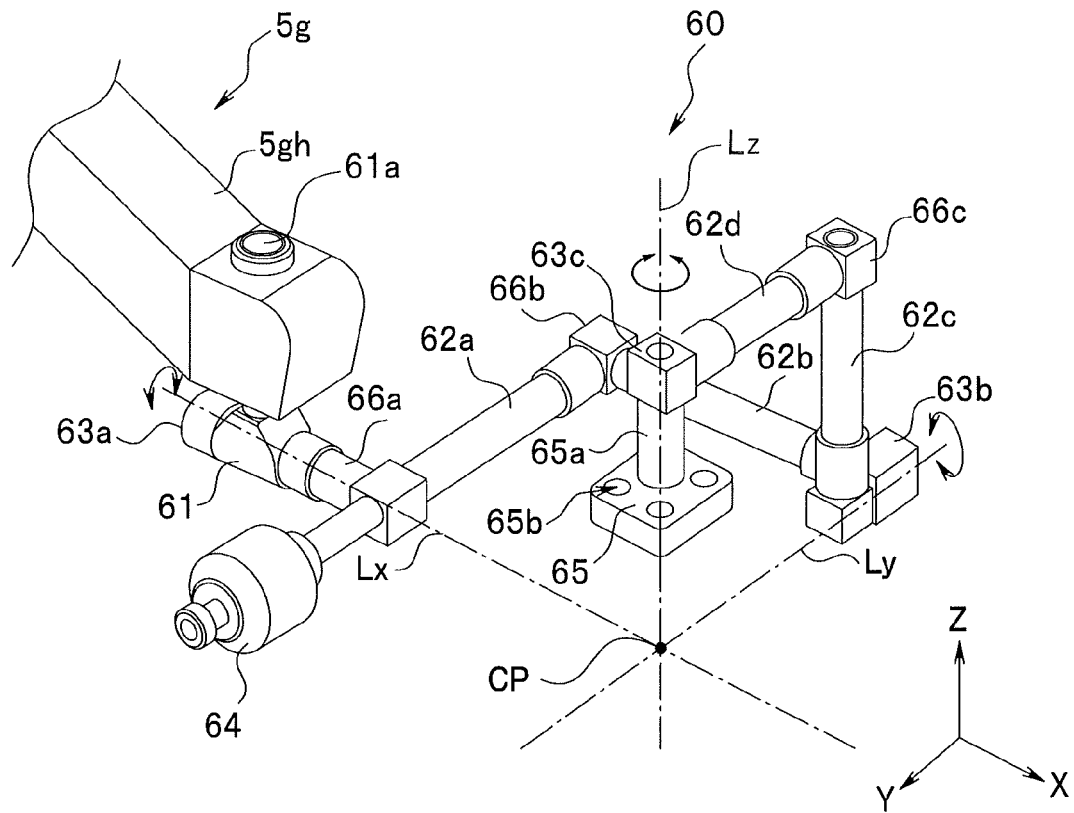
FIG. 8 is an illustration explaining a configuration of a driving device holder.

As shown in FIG. 8, the medical instrument holder 60 includes a rotation supporting portion 61, a plurality of arms 62, a plurality of rotation joints 63, a weight 64 and a fixing plate 65. Specifically, the medical instrument holder 60 includes the rotation supporting portion 61 having a first rotation joint 63a, a first arm 62a, a second arm 62b, a third arm 62c, a fourth arm 62d, a second rotation joint 63b and a third rotation joint 63c. The weight 64 is a so-called counter weight for offsetting the moment of inertia and arranged at an end portion of the first arm 62a.

The medical instrument holder 60 is rotatably attached to the horizontal arm portion 5gh through a rotation axis 61a provided at the rotation supporting portion 61. The first arm 62a is linked to the rotation supporting portion 61 through a first joint 66a.

The first arm 62a and the second arm 62b are linked with each other through a second joint 66b. The second arm 62b and the third arm 62c are rotatably attached to each other through the second rotation joint 63b. The third arm 62c and the fourth arm 62d are linked with each other through a third joint 66c. A projected portion 65a extending from one surface of the fixing plate 65 is rotatably attached to the fourth arm 62d through the third rotation joint 63c. Indicated by reference 65b is an escape hole into which a fixing screw is inserted. Four escape holes 65b are provided in the present embodiment. The escape holes 65b may be four or less.

The medical instrument holder 60 of the present embodiment is configured so as to have a cross-point CP which is approximate to a point intersected by a first rotation axis extension line Lx of the first rotation joint 63a, a second rotation axis extension line Ly of the second rotation joint 63b and a third rotation axis extension line Lz of the third rotation joint 63c, which are provided at the rotation supporting portion 61. The first rotation axis extension line Lx, the second rotation axis extension line Ly and the third rotation axis extension line Lz are configured to provide imaginary X axis, Y axis and Z axis, respectively.

Figure 9:
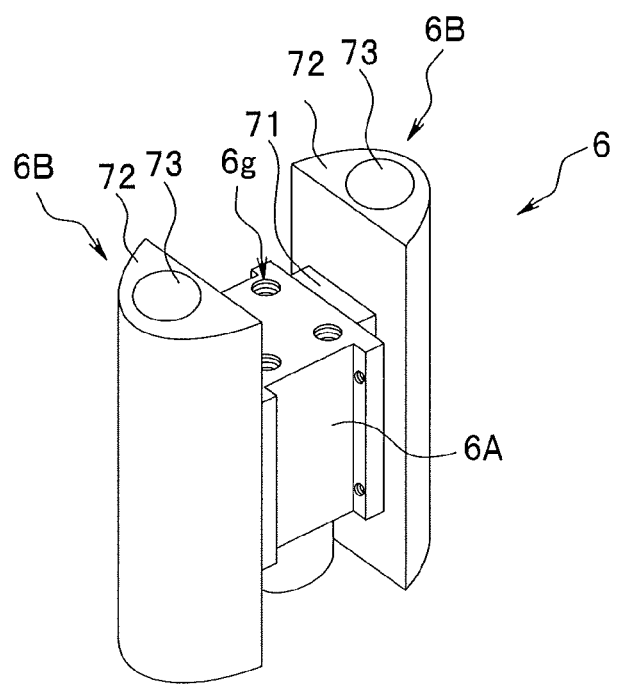
FIG. 9 is a perspective view explaining a configuration of a medical instrument fitting.
Figure 10:
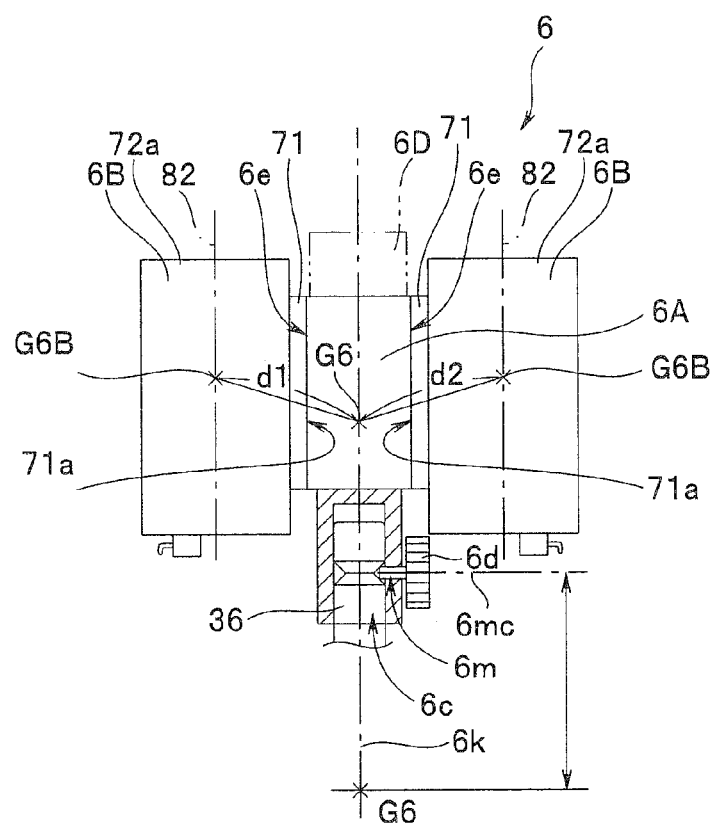
FIG. 10 is a side view, including a partial cross-sectional view, for explaining a configuration of the medical instrument fitting.

As shown in FIGS. 9 and 10, the medical instrument fitting 6 includes a fitting body 6A and two manipulator drive units 6B and 6B. A medical instrument fitting portion 6c for arranging the driver fixing portion 36 is formed in the fitting body 6A. Reference 6d indicates a fixing screw. The fixing screw 6d achieves integral fixation of the driver fixing portion 36 arranged at the medical instrument fitting portion 6c. A distal end of the fixing screw 6d is configured to have a tapered surface so as to be in close contact with both of inclined surfaces of the V-shaped groove 36v of the driver fixing portion 36.

In FIG. 9, indicated by reference 6g are screw holes provided in a top surface of the fitting body 6A. The screw holes 6g are formed so as to correspond to the respective escape holes 65b of the fixing plate 65.

Figure 11:
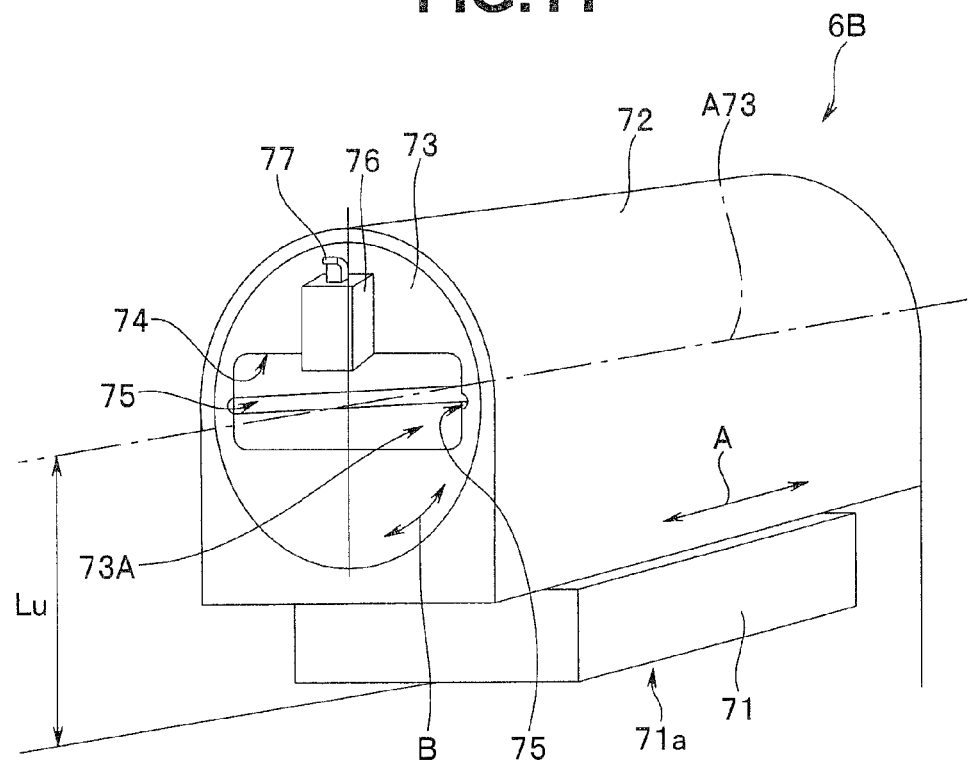
FIG. 11 is a perspective view explaining a configuration of a manipulator drive unit.
Figure 12:
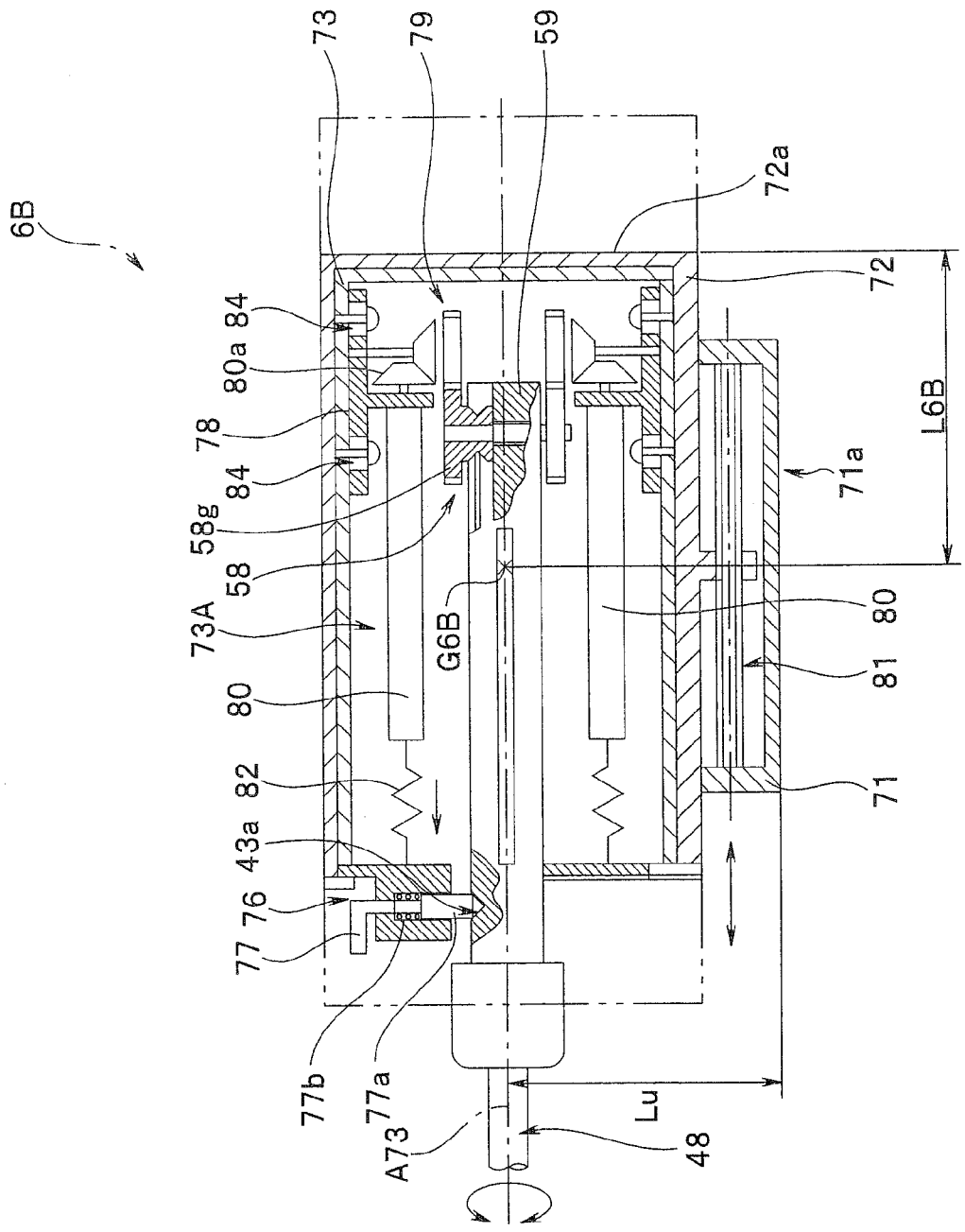
FIG. 12 is a cross-sectional view explaining a configuration of the manipulator drive unit.

As shown in FIGS. 11 and 12, each manipulator drive unit 6B includes a base portion 71, an advancing/retreating portion 72, a rolling portion 73 and a plurality of drive motors.

The advancing/retreating portion 72 configures the linear motion joint which is able to freely advance/retreat with respect to the base portion 71 as indicated by an arrow A. Specifically, a feed screw mechanism 81 is provided in the base portion 71. Upon actuation of the feed screw mechanism 81 by a first motor fixedly set up at a motor supporting portion, not shown, the advancing/retreating portion 72 including the rolling portion 73 is advanced/retreated. Then, the treatment portions 41 of the manipulators 3 and 4 are advanced or retreated.

The rolling portion 73 configures the roll drive joint which rotates about a roll axis A73. Specifically, the rolling portion 73 is configured to be rotatable, as indicated by an arrow B, with respect to the advancing/retreating portion 72. The rolling portion 73 is provided with a gear mechanism, not shown, for transmitting driving force. When a second motor fixedly set up at the motor supporting portion, not shown, is driven, the rotation driving force is transmitted to the gear mechanism. The rolling portion 73 is then rotated with respect to the advancing/retreating portion 72. Then, the manipulator insertion portion 48 extending from the manipulator connecting portion 43 is rotated about the roll axis A73.

The roll axis A73 of each manipulator drive unit 6B is set at a position distanced from a fitting reference surface 71a of the base portion 71 by a predetermined distance, i.e. a length Lu. The fitting reference surface 71a is placed at a fitting surface 6e of the fitting body 6A shown in FIG. 10. It is so configured that, when the fitting reference surface 71a is placed at the fitting surface 6e, the distance from the center axis of the fitting body 6A to the roll axis A73 coincides with the distance from the center axis of the over tube 20A to the first extension line 16.

Each rolling portion 73 has a manipulator connecting portion arranging space 73A in the interior thereof, and a connecting portion insertion hole 74 communicating with the arranging space 73A. The connecting portion insertion hole 74 has guiding grooves 75 for the insertion of the respective guiding portions 55 in an engaging manner. A connecting portion holder 76 is provided in the vicinity of the connecting portion insertion hole 74, to prevent the manipulator connecting portion 43 arranged in the arranging space 73A from dropping out of the arranging space 73A. The connecting portion holder 76 is provided with a retractable lever 77.

As shown in FIG. 12, upon completion of the connection between the manipulator 3 and the manipulator drive unit 6B, or between the manipulator 4 and the manipulator drive unit 6B, the manipulator connecting portion 43 is permitted placement in the arranging space 73A of the rolling portion 73. At this time, an engaging portion 77a integrated into the lever 77 is permitted placement in the click hole 43a by the bias force of a spring 77b. In the state where the connection has been completed, a rotation transmission gear mechanism 79 which is fixedly set at a motor support 78 provided in the arranging space 73A, engages with the spur gears 58g provided at the pulleys 58.

The arranging space 73A of the rolling portion 73 is provided therein with a plurality of wire motors 80 which are fixedly set at the motor support 78. When the wire motors 80 are driven, the rotation is transmitted to the spur gears 58g through gears 80g and the rotation transmission gear mechanism 79, so that the pulleys 58 can be rotated. Then, as described above, the angle wires 56 are tugged/relaxed in response to the rotation of the pulleys 58, whereby the position and the posture of the treatment portion 41 are changed.

Indicated by reference 82 are engaging springs for pulling the motors 80 fixed to the motor support 78 to the side of the connecting portion insertion hole 74. Thus, under the condition where the manipulator connecting portion 43 is not arranged in the arranging space 73A, the motor support 78 is shifted to the side of the connecting portion insertion hole 74 by a length corresponding to the allowance of long holes 84. In other words, the spur gears 58g of the pulleys 58 and the gears of the rotation transmission gear mechanism 79 are in the state of being disengaged.

With the insertion of the manipulator connecting portion 43 into the arranging space 73A, the spur gears 58g come into contact with the gears of the rotation transmission gear mechanism 79. Then, further movement of the manipulator connecting portion 43 allows the motor support 78 to move in the same direction together with the manipulator connecting portion 43, against the bias force of the engaging springs 82.

When the manipulator connecting portion 43 is arranged in a predetermined state in the arranging space 73A, the gears of the rotation transmission gear mechanism 79 and the spur gears 58g are retained in the state of being engaged with each other by the bias force of the engaging springs 82.

In each manipulator drive unit 6B configured in this way, the position of a center of gravity G6B of the manipulator drive unit 6B is adjusted so as to be positioned on the roll axis A73, being apart from a center-of-gravity reference surface 72a of the advancing/retreating portion 72 by a predetermined distance L6B.

Then, the manipulator drive units 6B configured in this way are attached to the fitting body 6A. In this case, the fitting reference surfaces 71a are brought into close contact with the respective fitting surfaces 6e, while the levels of the center-of-gravity reference surfaces 72a of the manipulator drive units 6B are permitted to coincide with each other, so as to achieve an integral attachment in a threaded manner, for example. In this way, the medical instrument fitting 6 is configured in which the manipulator drive units 6B are integrally fixed to the fitting body 6A shown in FIG. 10.

Confirmation is now made as to whether or not the center of gravity G6 of the medical instrument fitting 6 is positioned on an extension line 6k of the center axis of the medical instrument fitting portion 6c of the fitting body 6A (hereinafter referred to as a fourth extension line). When the center of gravity G6 of the medical instrument fitting 6 falls on the fourth extension line 6k, a configuration can be achieved in which distances d1 and d2 from the center of gravity G6 to the center of gravity G6B of the respective manipulator drive units 6B are equal to each other.

Figure 13:
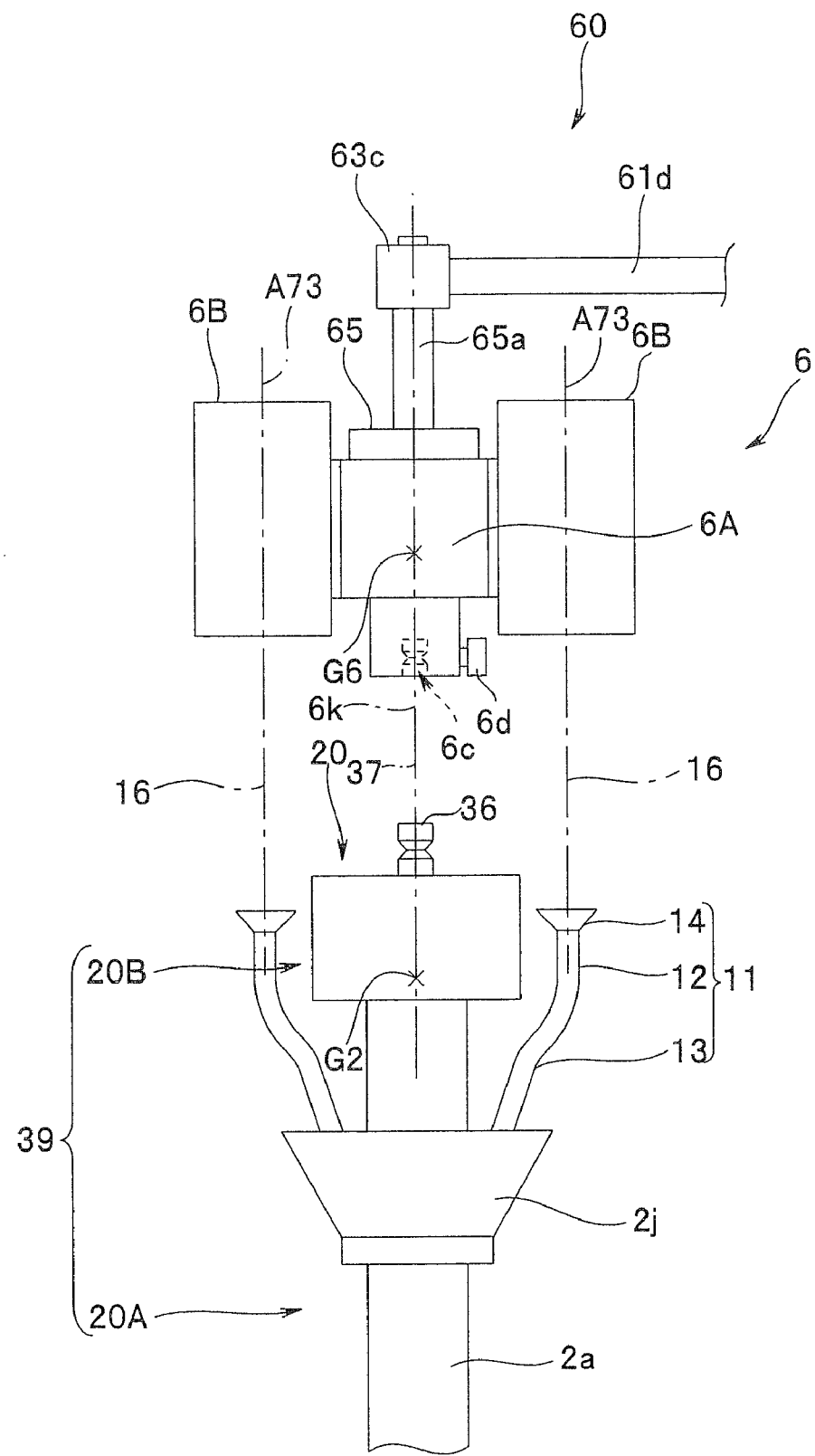
FIG. 13 is an illustration explaining a relationship between a medical instrument fitting attached to a driving device holder and an electric bending over tube.

Then, the medical instrument fitting 6 configured in this way is integrally fixed to the fixing plate 65 using a screw, not shown. Then, as shown in FIG. 13, the center axes of the fourth extension line 6k and the projected portion 65a align with each other. Thereafter, in order to attach the electric bending over tube 39 to the medical instrument fitting 6 which is integrated with the fixing plate 65, the driver fixing portion 36 is permitted to confront the medical instrument fitting portion 6c. In this case, alignment of the third extension line 37 with the fourth extension line 6k allows alignment of the first extension lines 16 with the respective roll axes A73.

In this way, the manipulator insertion portions 48 of the manipulators 3 and 4 attached to the respective manipulator drive units 6B can be smoothly inserted, through the respective guide pipes 11, into the manipulator holes 2f1 and 2f2 formed in the tube portion 2a.

Figure 14:
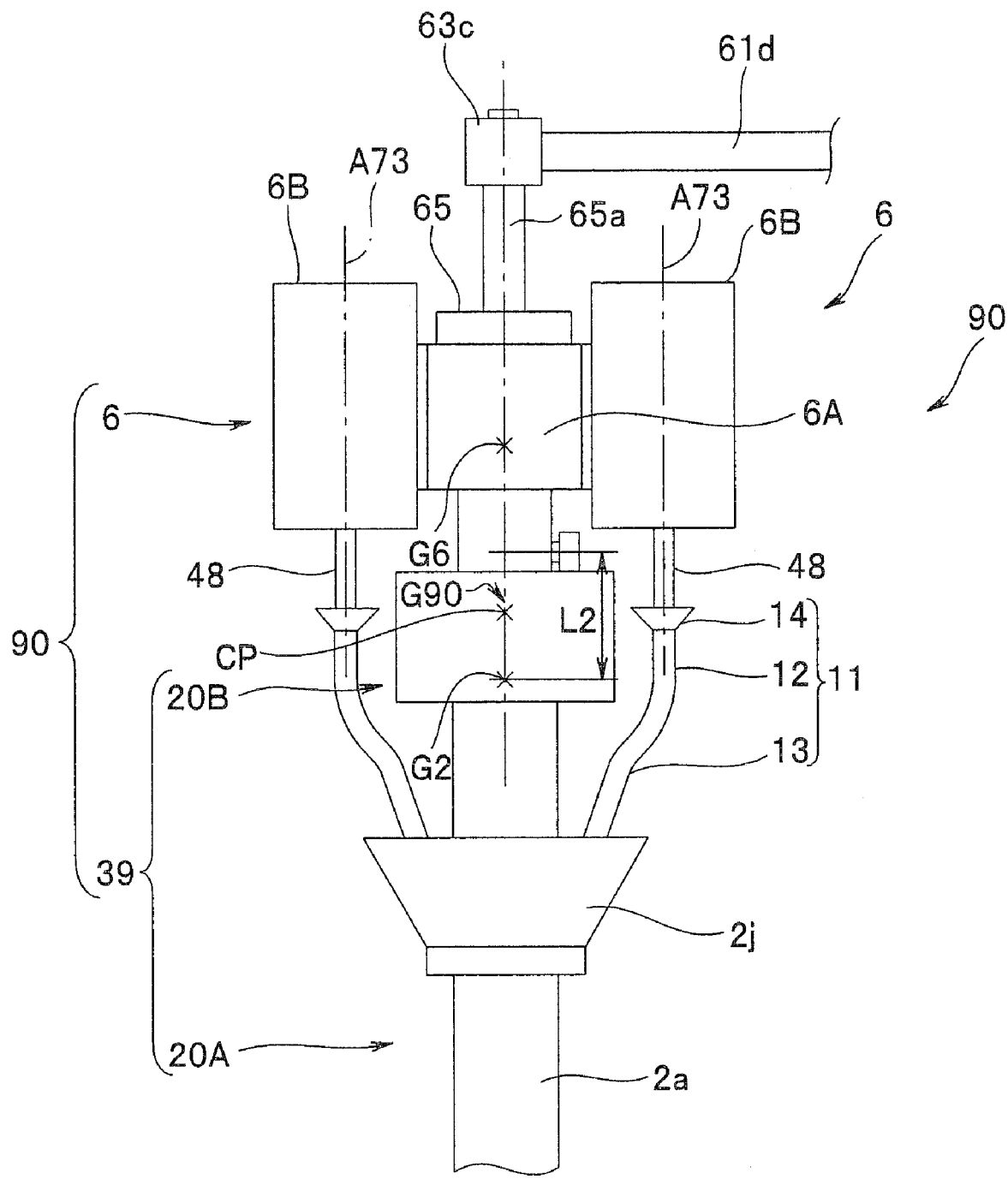
FIG. 14 is an illustration explaining a state where the electric bending over tube is attached to the medical instrument fitting which is attached to the driving device holder.

Then, as shown in FIG. 14, the electric bending over tube 39 is attached to the medical instrument fitting portion 6c of the medical instrument fitting 6 to configure an integrated device 90. In this case, the manipulator insertion portions 48 of the manipulators 3 and 4 connected to the respective manipulator drive units 6B can be arranged in the tube portion 2a in a predetermined state, without being bent.

Thus, the electric bending over tube 39, i.e. a medical instrument for conducting observation, and the manipulators 3 and 4, i.e. a plurality of medical instruments for conducting treatment, can be attached to the medical instrument holder 60 attached to the medical instrument holding device 5. This configuration may considerably reduce the length of the manipulator insertion portions of the manipulators.

Also, owing to the configuration in which each manipulator guide pipe is configured by a linear manipulator guiding portion and a curved manipulator introducing portion, with the first extension line of the manipulator guiding portion being aligned with the roll axis of the manipulator drive unit, the manipulator insertion portion of each manipulator can be smoothly introduced into each manipulator hole of the tube portion.

As a result, the driving force of the drive motors provided at the manipulator drive units can be reliably transmitted to the active joints provided at the manipulators to thereby obtain excellent operability.

Further, since the distances from the center of gravity of the medical instrument fitting to the centers of gravity of the individual manipulator drive units are ensured to be equal, the balance can be steadied between the electric bending over tube and the two manipulators to be attached to the medical instrument fitting. Accordingly, steady performance can be achieved in the observation conducted by the observation device provided at the over tube, and the treatment conducted by the treatment portions of the plurality of manipulators inserted into the over tube.

Figure 15:
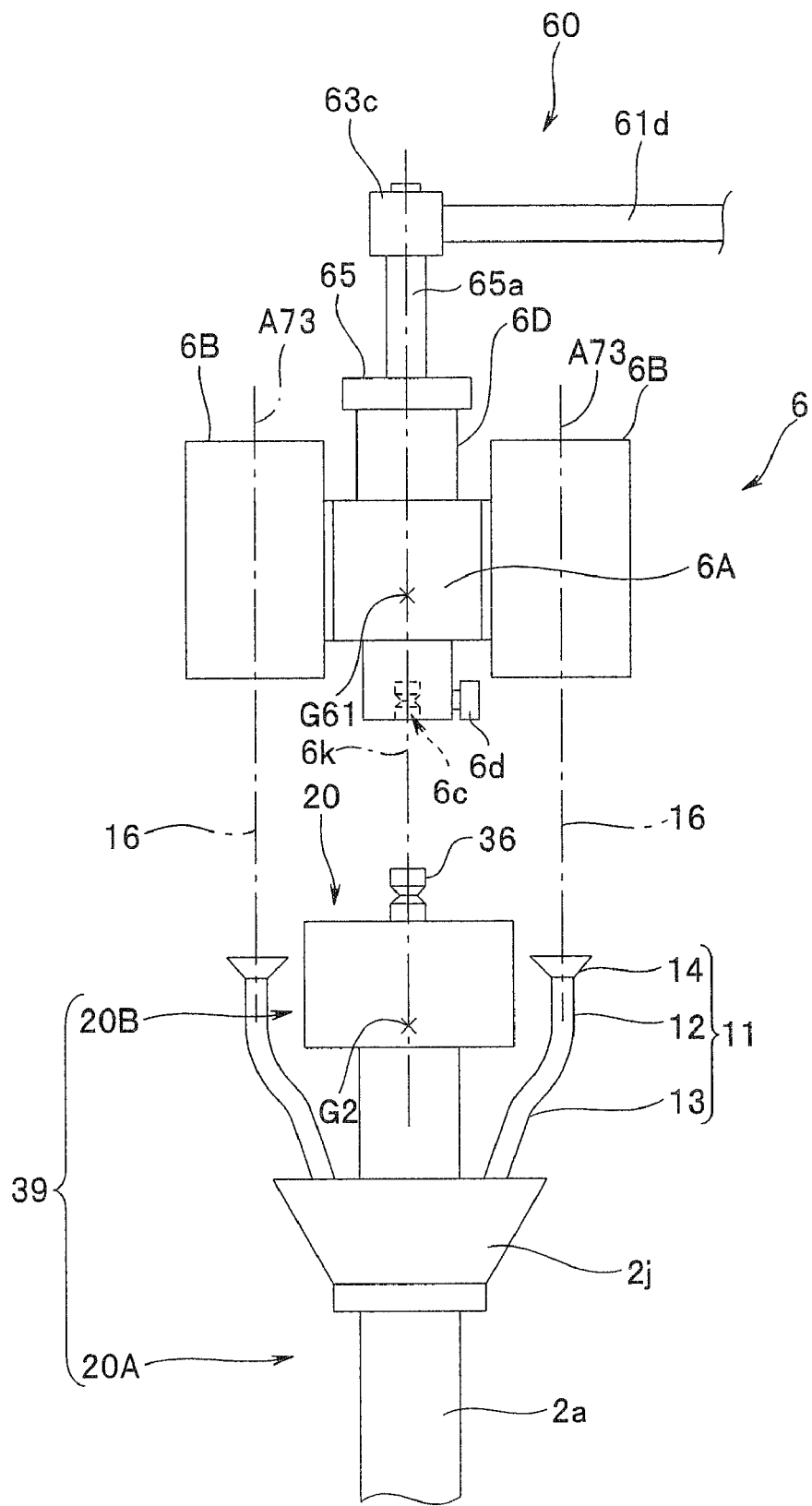
FIG. 15 is an illustration explaining a relationship between the medical instrument fitting attached to the driving device holder through an intermediate member and the electric bending over tube.

In the case where the center of gravity G6 of the fitting body 6A is deviated from the fourth extension line 6k when the manipulator drive units 6B are attached to the fitting body 6A, an intermediate member 6D shown by the dash-dot-dot line in FIG. 10 may be attached to the fitting body 6A. Then, as shown in FIG. 15, an adjusting operation may be performed so that a center of gravity G61 of the medical instrument fitting 6 having the intermediate member 6D can be positioned on the fourth extension line 6k. Thus, the same effects and advantages as those described above can be obtained.

Also, in the case where the intermediate member 6D is provided at the fitting body 6A and adjustment is performed to have the center of gravity G61 positioned on the fourth extension line 6k, the center of gravity of the integrated device 90 may be adjusted to be positioned on the fourth extension line 6k. In other words, the intermediate member 6D, whose length has been adjusted, may be provided at the fitting body 6A, so that the center of gravity G90 shown in FIG. 14 may coincide with the cross-point CP.

In this way, by providing an intermediate member to permit the center of gravity G90 to coincide with the cross-point CP, the rotation moment that would be generated by separating the center of gravity from the cross-point CP can be eliminated to thereby further enhance the operability for the operator to operate the integrated device. It should be noted that reference 8 indicates a tube bending portion operating device. The tube bending portion operating device 8 plays a roll of performing a bending operation of the tube bending portion 2g of the over tube 20A, with a joy stick 8j being provided. An inclining operation of the joy stick 8j can drive the motors 32 provided at the over tube driver 20B. Then, the driving force of the motors 32 is transmitted to the bending operation wires through the gear head shaft 33, the motor-side cap gears 34, the transmission-side cap gears 30, the coupling supports 29 and the couplings 2s, for vertical or lateral bending of the tube bending portion 2g.

It is so configured that the positions and the postures of the treatment portions 41 of the manipulators 3 and 4 are operated in response to the operations of master portions 9A and 9B provided at the manipulator operating device 9 shown in FIG. 2.

Specifically, the manipulator operating device 9 includes a grasping-tool master portion 9A and a high-frequency master portion 9B. The master portions 9A and 9B serve as an input device for setting the joint angles, axial positions, projection lengths and the like of the plurality of joints 52 and 53 possessed by the first manipulator 3 and the second manipulator 4.

The master portions 9A and 9B are provided with master-side joint pieces 9c, 9d, 9e and 9f, a master-side hand arm 9h and a master-side knife arm 9k, which correspond to the manipulators 3 and 4.

The observation control unit 7 includes an illumination portion and an image processor. The illumination portion supplies power to light emitting elements, such as an illumination probe or an LED for an endoscope, or transmits illumination light of the illumination lamp for an illumination optical system of an endoscope. The image processor includes: a drive circuit for driving an observation probe, or a solid image pick up device, such as a CCD or CMOS, incorporated in a distal end portion of an endoscope; and an image processing circuit for generating a video signal from the image signal transmitted from the solid image pick up device after being subjected to photo-electric conversion. The video signal generate by the image processing circuit of the image processor is outputted to a display 7a to display an endoscopic image on a screen 7b.

Further, the manipulator control unit 10 is electrically connected to the manipulator operating device 9 and the manipulator drive units 6B. Reference 10a indicates a manipulator-side monitor.

In the embodiment described above, two manipulator drive units 6B are provided as the plurality of manipulator drive units provided at the medical instrument fitting 6. However, the number of the manipulator drive units 6B provided at the medical instrument fitting 6 is not limited to two, but may be three, as shown in FIG. 16, or more.

Figure 16:
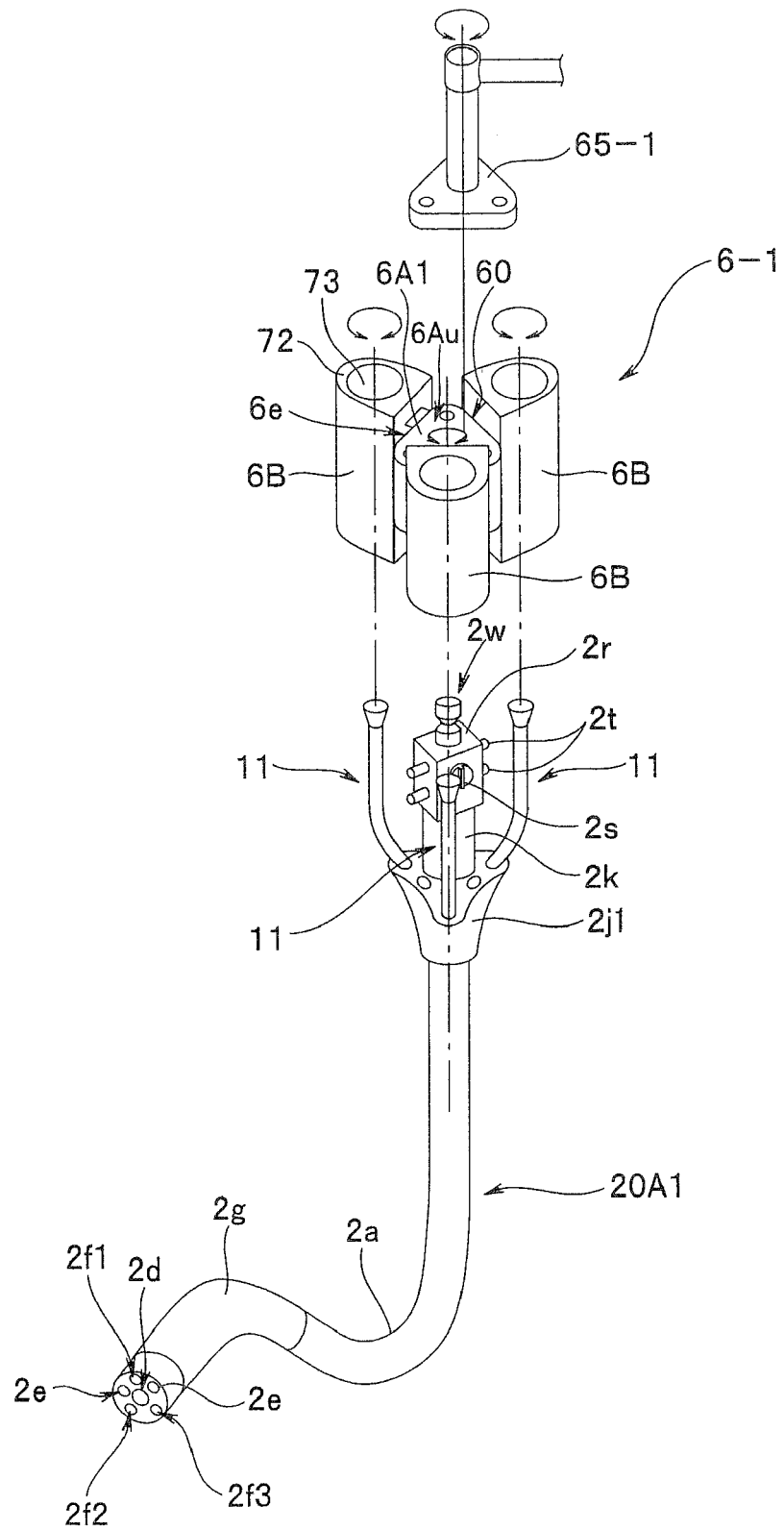
FIG. 16 is an illustration explaining a relationship between a medical instrument fitting having three manipulator drive units and the over tube.

As shown in FIG. 16, a medical instrument fitting 6-1 of the present embodiment is provided with a fitting body 6A1 having three fitting surfaces 6e. Each of the three fitting surfaces 6e is adapted to be attached with the manipulator drive unit 6B having a configuration as described above. The medical instrument fitting 6-1 is attached to a fixing plate 65-1 which is configured to have a substantially triangular shape similar to a top surface 6Au of the fitting body 6A1. Further, an over tube 20A1 is provided with manipulator holes 2f1, 2f2 and 2f3 through which three manipulators can be inserted. Three manipulator guide pipes 11 are arranged at a communicating portion 2j 1 to communicate with the respective manipulator holes 2f1, 2f2 and 2f3. The remaining configuration is the same as the embodiment described above. The same references are designated to the same members for omission of the explanation.

In the embodiment described above, the first medical instrument is the over tube through which an observation probe is inserted. However, as shown in FIGS. 17 and 18, the first medical instrument may be an endoscope 100 having a plurality of treatment instrument channels 101 and 102.

Figure 17:
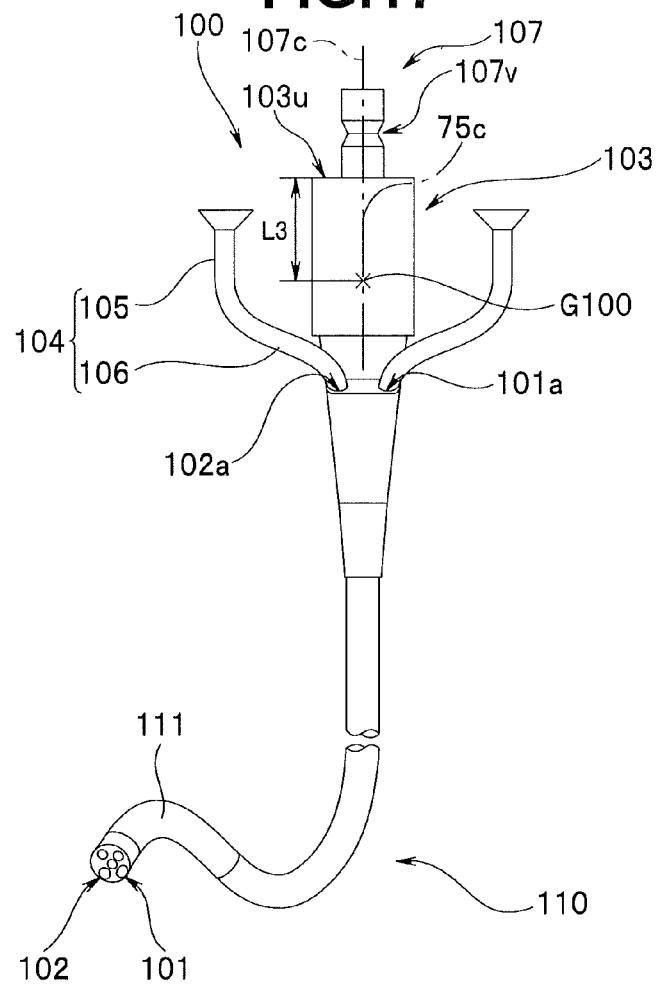
FIG. 17 is an illustration of an endoscope, as viewed from the front, which serves as a first medical instrument having treatment instrument channels at an insertion portion.
Figure 18:
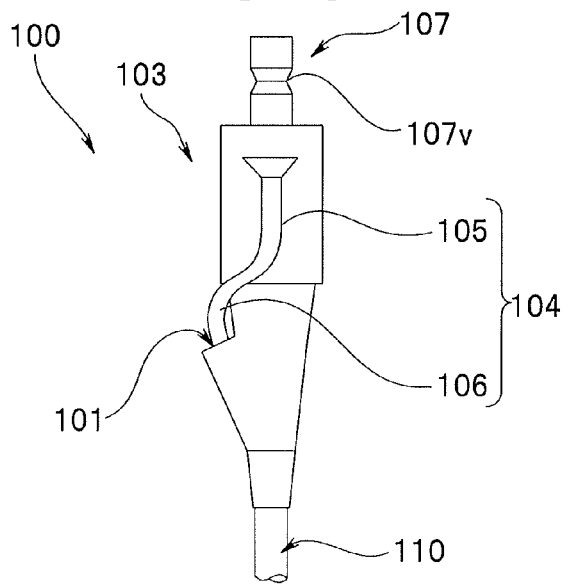
FIG. 18 is an illustration of the endoscope illustrated in FIG. 17, as viewed from the side.

As shown in FIGS. 17 and 18, the endoscope 100 includes a holding portion 103 having two treatment instrument insertion holes 101a and 102a. An endoscope manipulator guide pipe 104 having substantially the same configuration as the manipulator guide pipe 11 is arranged at each of the treatment instrument insertion holes 101a and 102a. Each endoscope manipulator guide pipe 104 includes a manipulator guiding portion 105 having a linear shape and a manipulator introducing portion 106 having a curved shape.

A projected endoscope fixing portion 107 is integrally provided at the holding portion 103. The endoscope fixing portion 107 is provided with a V-shaped groove 107v having a configuration similar to that of the driver fixing portion 36. The holding portion 103 is provided therein with drive motors (not shown) for driving endoscope bending portion wires, by which a bending portion 111 configuring an insertion portion 110 of the endoscope 100 can be bent.

Figure 19:
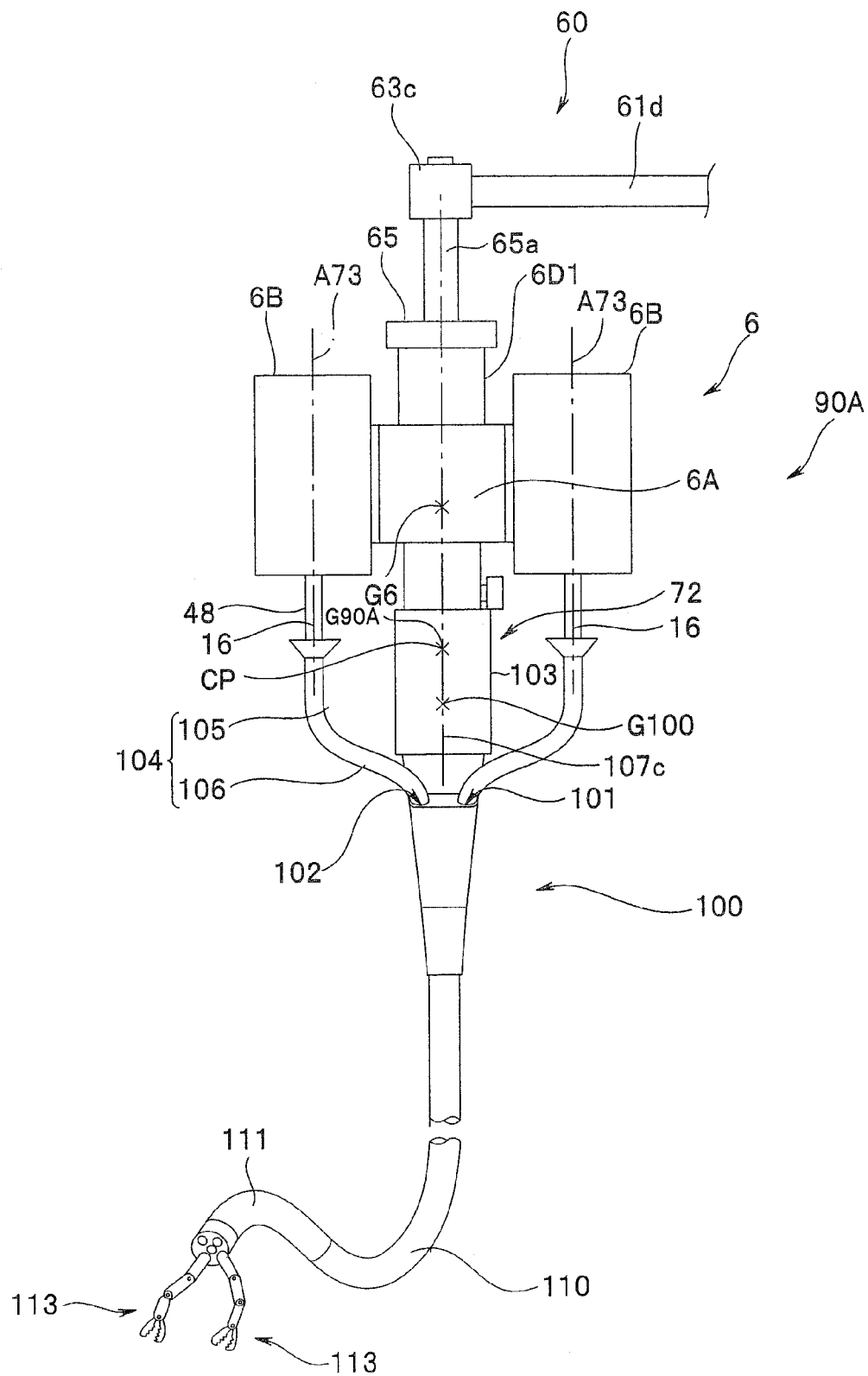
FIG. 19 is an illustration explaining a relationship between the medical instrument fitting attached to a driving device holder through an intermediate member, and the endoscope.

A center of gravity G100 of the endoscope 100 is set, in advance, at a position on a center axis 107c of the endoscope fixing portion 107, being apart from a top end face 103u by a predetermined distance, e.g. by a distance L3. As shown in FIG. 19, an integrated device 90A can be configured, in which the endoscope 100 and the medical instrument fitting 6 are integrated with each other. In this case, the center axis 107c aligns with the center axis of a projected portion 65a. Also, the first extension line 16 of the manipulator guiding portion 105 aligns with the roll axis A73.

Indicated by reference 113 are grasping manipulators. The remaining configuration is the same as in the embodiment described above. The same references are designated to the same members for omission of the explanation.

In this way, by providing the endoscope with the endoscope fixing portion corresponding to the medical instrument fitting portion, the endoscope and the plurality of manipulators can be attached to an endoscope holding device through the medical instrument fitting. Other effects and advantages are the same as those in the embodiment described above.

In fixing the integrated device 90A, which is an integration of the medical instrument fitting 6 and the endoscope 100, to the fixing plate 65, an intermediate member 6D1 may be arranged, as shown in FIG. 19, to permit the position of the center of gravity G90A of the integrated device 90A to coincide with the cross-point CP of the medical instrument holder 60.

In this way, in the same manner as described above, the rotation moment that would be generated by separating the center of gravity from the cross-point CP can be eliminated to thereby enhance the operability for the operator.

Figure 20:
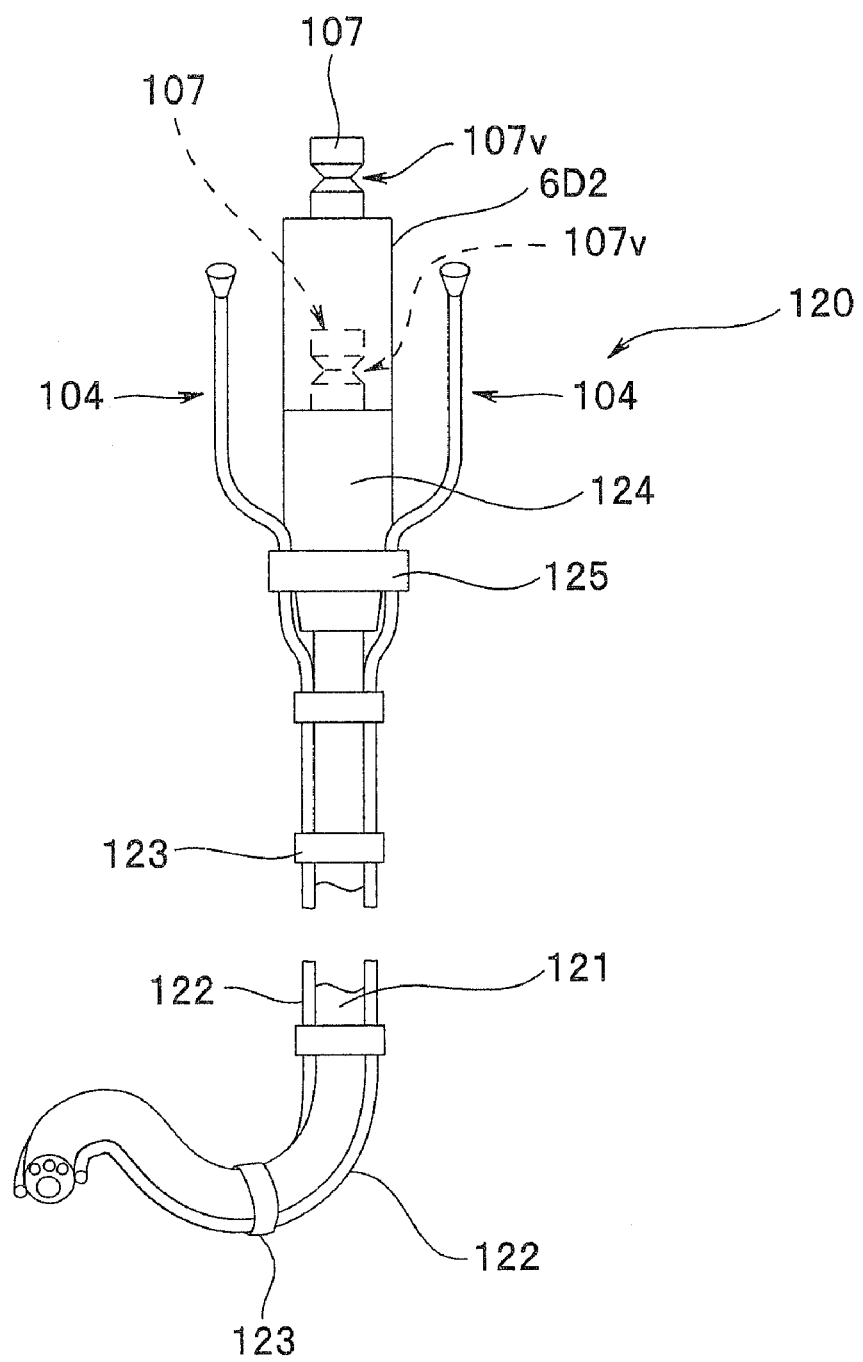
FIG. 20 is an illustration explaining an endoscope having an insertion portion provided with external channels for treatment instruments.

As shown in FIG. 20, the endoscope may be an endoscope 120 with an insertion portion 121 which is provided with external channels 122 for treatment instruments. The external channels 122 are attached to the insertion portion 121 by means of fixing belts 123. The external channels 122 for treatment instruments, which are located on the side of a holding portion 124 are fixed to the holding portion 124 by means of a guide pipe support member 125 that is a support member for the second medical instrument guiding members.

Then, the endoscope manipulator guide pipes 104 are arranged at the guide pipe support member 125. Thus, the same effects and advantages as described above can be obtained.

In the endoscope 120, the position of the center of gravity is different from that of the endoscope 100. Thus, in the endoscope 120, the position of the center of gravity is set, in advance, on the center axis of an endoscope fixing portion 126. Then, an intermediate member 6D2 may be arranged to have the position of a center of gravity G120 coincided with the cross-point CP. In this case, the intermediate member 6D2 includes the endoscope fixing portion 107, and a hole for arranging the endoscope fixing portion 107 provided at the holding portion 124, which hole is the same as the one for the medical instrument fitting portion 6c.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric medical instrument fitting which is attached to a medical instrument holding device, comprising:
 a medical instrument holder provided to a holding portion of the medical instrument holding device, the medical instrument holder including:
  a plurality of arms:
  a first rotation joint which rotatably links the arms and rotates about a first rotation axis, as an imaginary X axis;
  a second rotation joint which rotatably links the arms and rotates about a second rotation axis, as an imaginary Y axis;
  a third rotation joint which rotatably links the arms and rotates about a third rotation axis, as an imaginary Z axis;
  a cross-point where an extension line of the first rotation axis, an extension line of the second rotation axis and an extension line of the third rotation axis intersect at one point; and
 a fitting body of the electric medical instrument fitting, the fitting body including:
 a fitting portion that is capable of attachment/detachment of a first medical instrument which is provided with an observation device and has channel holes for inserting treatment instruments;
  a plurality of fitting surfaces on which a plurality of second medical instrument drive units are respectively provided fixedly for a plurality of second medical instruments: each of the drive units being detachably connectable with a drive connecting portion provided at a proximal portion of each second medical instrument which is provided with a treatment portion on the side of a distal end of an insertion portion to be inserted into each channel hole; having a joint driver, an advancing/retreating driver and a rotation driver for changing position and posture of each treatment portion to be connected; and having a center of gravity positioned at a predetermined position on a roll axis of the rotation driver, and
 a surface having screw holes for arranging an intermediate member which makes a center of gravity of an entirety of the fitting body coincide with the cross-point of the medical instrument holder on an extension line of a center axis of the fitting portion in a state where the first medical instrument is attached to the fitting portion and the second medical instruments are respectively connected with the plurality of second medical instrument drive units which are provided fixedly on the fitting surfaces,
 wherein the medical instrument holder has an intermediate member fixing plate which is provided at the arm connected with the third rotation joint and to which the intermediate member is attached, and the fitting body of the electric medical instrument fitting is connected with the intermediate member fixing plate.

2. The electric medical instrument fitting according to claim 1, wherein:
 the first medical instrument is an electric observation device comprising a medical bending tube and a tube driver.

3. The electric medical instrument fitting according to claim 2, wherein:
 the medical bending tube comprises:
 a tube portion having a plurality of channel holes including a channel hole for arranging the observation device and channel holes for arranging insertion portions of the second medical instruments, and having a bending portion midway;

a housing portion provided at a proximal end of the tube portion, the housing portion having: couplings for tugging/relaxing bending operation wires each having one end which is fixed to the bending portion and a proximal end which is wound about a pulley; and a medical bending tube fixing portion attached to the tube bending portion;

a guiding portion arranged between the housing portion and the tube portion and provided with openings for guiding holes which communicate with the respective plurality of channel holes provided at the tube body; and second medical instrument guiding members configured by hard pipe members each having: a linear manipulator guiding portion provided at an orifice to introduce an insertion portion of each second medical instrument into each channel hole, and arranged so that a center axis thereof aligns with an extension line of the roll axis; and a manipulator introducing portion whose one end portion communicates with the hole of the linear portion and the other end portion communicates with the channel hole to prevent the insertion portion from being bent.

4. The electric medical instrument fitting according to claim 3, wherein:

the housing portion further comprises a center-of-gravity adjusting mechanism, the center-of-gravity adjusting mechanism comprising:

a balancer; and center-of-gravity adjusting screws for changing the position of the balancer in order to adjust the position of the center of gravity of the medical bending tube to a position on an extension line of the center axis of the medical bending tube fixing portion.

5. The electric medical instrument fitting according to claim 2, wherein:

the tube driver comprises:

a driver body, the driver body comprising:

a medical bending tube attaching portion to which the medical bending tube fixing portion is attached;

drive motor arranging portions each for arranging a drive motor that generates driving force for tugging the bending operation wire;

rotation transmission portion arranging portions each for arranging a rotation transmission mechanism for transmitting the driving force of the drive motor to the coupling; and an outer cover having a driver fixing portion to be attached to the fitting portion of the fitting body, and having a center of gravity set, in advance, on an extension line of the axis of the driver fixing portion.

6. The electric medical instrument fitting according to claim 1, wherein:

the first medical instrument is an endoscope which is provided with an observation optical system at an endoscope insertion portion thereof, the endoscope comprising:

a fixing portion which is provided at a holding portion connected to the endoscope insertion portion so as to be attached to the fitting portion of the fitting body;

channel holes provided along the longitudinal axis of the endoscope insertion portion, to which the insertion portions of the plurality of second medical instruments are inserted; and second medical instrument guiding members configured by hard pipe members each having: a linear manipulator guiding portion linked to each channel hole to introduce an insertion portion of each second medical instrument into each channel hole, and arranged so that a center axis thereof aligns with an extension line of the roll axis; and a manipulator introducing portion whose one end portion communicates with the hole of the linear portion and the other end portion communicates with the channel hole to prevent the insertion portion from being bent.

7. The electric medical instrument fitting according to claim 1, wherein:

the first medical instrument is an endoscope which is provided with an observation optical system at an endoscope insertion portion thereof, the endoscope comprising:

a fixing portion which is provided at a holding portion connected to the endoscope insertion portion so as to be attached to the fitting portion of the fitting body;

a plurality of external channels having channel holes for inserting the insertion portions of the respective plurality of second medical instruments, the external channels being arranged along the longitudinal axis of the endoscope insertion portion using a fixing member;

second medical instrument guiding members configured by hard pipe members each having: a linear manipulator guiding portion linked to each channel hole to introduce an insertion portion of each second medical instrument into each channel hole of the external channels, and arranged so that a center axis thereof aligns with an extension line of the roll axis; and a manipulator introducing portion whose one end portion communicates with the hole of the linear portion and the other end portion communicates with the channel hole to prevent the insertion portion from being bent; and a support member for the second medical instrument guiding members for fixing the second medical instrument guiding members to the holding portion.

8. The electric medical instrument fitting according to claim 1, wherein a position of the center of gravity of each of the second medical instrument drive units is set to the predetermined position on the roll axis of the rotation driver, and a position of the roll axis is set apart from a fitting surface by a predetermined distance in a state where each of the drive units is attached to the fitting surface of the fitting body.

9. The electric medical instrument fitting according to claim 8, wherein:

the insertion portions of the plurality of second medical instruments are each defined starting from an axial center of an axis linking between the treatment portion and the manipulator bending portion, to an end face of the drive connecting portion, the longitudinal dimension being the same between the plurality of second medical instruments.

10. The electric medical instrument fitting according to claim 1, wherein:

the intermediate member also serves as an adjusting member for permitting the position of the center of gravity of the first medical instrument attached to the fitting body to coincide with the cross-point of the medical instrument holder.

* * * * *